United States Patent
Qi

(10) Patent No.: US 9,259,146 B2
(45) Date of Patent: Feb. 16, 2016

(54) BINOCULAR VISUAL PERFORMANCE MEASURING METHOD, BINOCULAR VISUAL PERFORMANCE MEASURING PROGRAM, EYEGLASS LENS DESIGN METHOD AND EYEGLASS LENS MANUFACTURING METHOD

(75) Inventor: Hua Qi, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 296 days.

(21) Appl. No.: 13/283,110

(22) Filed: Oct. 27, 2011

(65) Prior Publication Data

US 2012/0105609 A1 May 3, 2012

(30) Foreign Application Priority Data

Oct. 29, 2010 (JP) .................. 2010-243499
Oct. 29, 2010 (JP) .................. 2010-243500

(51) Int. Cl.
*A61B 3/00* (2006.01)
*A61B 3/08* (2006.01)

(52) U.S. Cl.
CPC ............. *A61B 3/08* (2013.01); *Y10T 29/49764* (2015.01)

(58) Field of Classification Search
CPC ............................... H04N 13/04; B23Q 17/00
USPC ........... 348/54, E13.026, E17.001; 29/407.01
See application file for complete search history.

(56) References Cited

U.S. PATENT DOCUMENTS 7,367,675 B2 5/2008 Maddalena et al.
2004/0105073 A1 6/2004 Maddalena et al.

2011/0205491 A1* 8/2011 Koiwa et al. .................. 351/206
2012/0050681 A1* 3/2012 Bonnin et al. ................. 351/210
2012/0081661 A1 4/2012 Yamakaji

FOREIGN PATENT DOCUMENTS

| JP | A-11-197107 | 7/1999 |
| JP | A-2004-537331 | 12/2004 |
| JP | A-2009-273869 | 11/2009 |
| JP | A-2010-075755 | 4/2010 |

(Continued)

OTHER PUBLICATIONS

US patent publication of WO 2010090144 A1.*

(Continued)

*Primary Examiner* — Jay Au Patel
*Assistant Examiner* — Frank Huang
(74) *Attorney, Agent, or Firm* — Oliff PLC

(57) ABSTRACT

A binocular visual performance measuring method including: a parallax image displaying step of displaying left and right parallax images at a predetermined measurement start position on a display screen when a measurement item is designated; a parallax image changing step of changing one of the left and right parallax images relative to the other of the left and right parallax images in accordance with the designated measurement item; a timing detecting step of detecting a timing when the subject viewing the left and right parallax images from a position a predetermined distance away from the display screen becomes unable to achieve fusion of the left and right parallax images; and a measurement value calculating step of calculating a measurement value of the designated measurement item based on the predetermined distance and a difference between the left and right parallax images defined at the detected timing.

16 Claims, 17 Drawing Sheets

(56) References Cited

FOREIGN PATENT DOCUMENTS

| JP | A-2010-099335 | 5/2010 |
| WO | WO 2010/090144 A1 | 8/2010 |
| WO | WO 2010090144 A1 * | 8/2010 |

OTHER PUBLICATIONS

Ishihara, "Little pupil science," 17th revised version, Kanehara & Co., Ltd., pp. 39, 41 and 49-51, 1925.

Hatada, "Depth information and a characteristic of a vision," Visual Information Research Group, p. 1-17, Apr. 23, 1974.

Notification of Reasons for Rejection dated Jul. 8, 2014 from Japanese Patent Application No. 2010-243499 (with English-language translation).

Notification of Reasons for Rejection dated Jul. 7, 2014 from Japanese Patent Application No. 2010-243500 (with English-language translation).

* cited by examiner

BINOCULAR VISUAL PERFORMANCE MEASURING METHOD, BINOCULAR VISUAL PERFORMANCE MEASURING PROGRAM, EYEGLASS LENS DESIGN METHOD AND EYEGLASS LENS MANUFACTURING METHOD

BACKGROUND OF THE INVENTION

The present invention relates to a method and a program for measuring binocular visual performance, and design and manufacturing methods for designing and manufacturing eyeglass lenses using the measurement result.

One of eyesight test items, a binocular visual performance test is known. The binocular visual performance test includes a simultaneous perception test, a fusion test and a stereoscopic viewing test. Eyesight tests of this type are described in Japanese Patent Provisional Publications No. 2010-99335A (hereafter, referred to as patent document #1) and No. 2010-75755A (hereafter, referred to as patent document #2).

The stereoscopic viewing test described in patent document #1 is performed using a HMD (Head Mounted Display). Specifically, a subject views an object as a virtual image wearing the HMD on one eye, and simultaneously views the object with the other eye as naked vision. The subject perceives retinal images of the object as a three dimensional object when the object viewed as the virtual image and the object viewed with the naked eye are in Panum's fusional area although the retinal images are not at corresponding points. In the test, the virtual image is moved from a state where the subject is able to perform stereoscopic viewing, so as to change binocular parallax. As the binocular parallax changes, the left and right retinal images deviate from the Panum's fusional area at a certain point in time. At this time, the subject perceives a double image of the object. As described above, the stereoscopic viewing test in patent document #1 performs a test of the stereoscopic viewing by measuring a breaking point which allows the subject to achieve the fusion for the object.

In an ophthalmologic testing method described in patent document #2, the binocular visual performance is tested using an indicator projected on a shallow hemisphere screen of an ophthalmologic testing apparatus. For example, in the fusion test, an image for a left eye and an image for a right eye are projected to overlap with each other so that the images can be recognized as a single image. Then, the two projected images are moved to depart from each other. In the ophthalmologic testing method described in patent document #2, a breaking point at which the shifted two images are recognized as a double image is measured to perform the fusion test.

SUMMARY OF THE INVENTION

Incidentally, the HMD is strict about the size and weight. Therefore, it is difficult to mount a large size display device on the HMD. For this reason, a general HMD is designed such that a focal length of an eyepiece is short and to have a wide viewing angle, so as to enlarge and project an image of the display device having the limited size. However, in compensation for configuring the eyepiece to have a wide viewing angle, a large degree of deterioration of image quality is caused by aberrations. In particular, a large degree of distortion is caused in a peripheral part of the image. When the deterioration of image quality is large, the subject might not be able to recognize the object of the virtual image and the object viewed with the naked eye as the same image. That is, the stereoscopic viewing test described in patent document #1 may cause double vision within an range in which the subject is essentially is able to achieve the fusion. As a result, a problem arises that the reliability of the measured value is low.

For implementing the ophthalmologic testing method described in patent document #2, it is essential to use a dedicated ophthalmologic testing apparatus. However, such an ophthalmologic testing apparatus is very expensive, and it is not easy to adopt such an ophthalmologic testing apparatus for the tests of the binocular visual performance. In addition, in the actual motion of an eye ball, a plurality of types of binocular visual performance acts in combination. However, the stereoscopic viewing test in patent document #2, it is impossible to measure the plurality of types of binocular visual performance acting in combination because the stereoscopic viewing test in the patent document #2 is based on the premise that an individual item concerning the binocular visual performance is independently measured.

The present invention is advantageous in that it provides at least one of a binocular visual performance measuring method, a binocular visual performance measuring program, an eyeglass lens design method and a eyeglass lens manufacturing method, suitable for measuring the binocular visual performance with a high degree of precision while suppressing cost.

According to an aspect of the invention, there is provided a binocular visual performance measuring method for measuring binocular visual performance using a stationary 3D video monitor having a display screen on which images for enabling a subject to perform stereoscopic viewing through binocular parallax are displayed. The method includes: a parallax image displaying step of displaying left and right parallax images at a predetermined measurement start position on the display screen when a measurement item of the binocular visual performance is designated; a parallax image changing step of changing one of the left and right parallax images relative to the other of the left and right parallax images in accordance with the designated measurement item; a timing detecting step of detecting a timing when the subject viewing the left and right parallax images from a position a predetermined distance away from the display screen becomes unable to achieve fusion of the left and right parallax images; and a measurement value calculating step of calculating a measurement value of the designated measurement item based on the predetermined distance and a difference between the left and right parallax images defined at the detected timing.

When the binocular visual performance is measured, preparing at least one general-purpose PC and one video monitor and installing the binocular visual performance measuring program onto the general-purpose PC suffices for measurement of the binocular visual performance. Therefore, according to the invention, the introduction cost can be suppressed considerably. Furthermore, the video monitor used for measurement of the binocular visual performance is configured not to require a strong power lens, such as a lens mounted on HMD. Therefore, decrease of the measurement accuracy due to distortion of the image can be suppressed. By appropriately setting change to be given to the image (movement, rotation, change of magnification), it becomes possible to easily measure the various types of parameters concerning the binocular visual performance.

In at least one aspect, the binocular visual performance measuring method may further include: a start position changing step of changing the predetermined measurement start position each time the measurement value is calculated. In the parallax image changing step, the timing detecting step and the measurement value calculating step are executed in this order while displaying the left and eight parallax images at the changed predetermined measurement position, and the measurement value is obtained for the designated measurement item for each of the changed predetermined measurement start positions.

With this configuration, the measurement value of the designated measurement item can be obtained for each of the different measurement start positions. Therefore, the measurement result can be obtained for each of different visual axis directions.

In at least one aspect, the designated measurement item is a relative convergence. In this case, in the parallax image changing step, the left and right parallax images are shifted in a horizontal direction on the display screen to approach to or depart from each other. In the measurement value calculating step, the relative convergence of the subject is calculated based on the predetermine distance and a position shift amount in the horizontal direction between the left and right parallax images defined at the detected timing.

In at least one aspect, the designated measurement item is a left and right eye vertical divergence permissible value which is a permissible value of a vertical divergence of left and right eyes capable of performing stereoscopic viewing. In the parallax image changing step, the left and right parallax images are shifted in a vertical direction on the display screen to approach to or depart from each other. In the measurement value calculating step, the left and right eye vertical divergence permissible value of the subject is calculated based on the predetermine distance and a position shift amount in the vertical direction between the left and right parallax images defined at the detected timing.

In at least one aspect, the designated measurement item is a first unequal magnification permissible value which is a permissible value of an unequal magnification of left and right eyes capable of performing stereoscopic viewing. In the parallax image changing step, a display magnification of at least one of the left and right parallax images is changed in a fixed aspect ratio so that display magnifications of the left and right parallax images change relative to each other. In the measurement value calculating step, the first unequal magnification permissible value of the subject is calculated based on the predetermine distance and a ratio between the display magnifications of the left and right parallax images defined at the detected timing.

In at least one aspect, the designated measurement item is a second unequal magnification permissible value which is a permissible value of an unequal magnification defined in a particular direction for left and right eyes capable of performing stereoscopic viewing. In the parallax image changing step, a display magnification of at least one of the left and right parallax images is changed only in the particular direction so that display magnifications of the left and right parallax images change relative to each other in the particular direction. In the measurement value calculating step, the second unequal magnification permissible value of the subject is calculated based on the predetermine distance and a ratio between the display magnifications of the left and right parallax images defined at the detected timing.

In at least one aspect, the designated measurement item is a left and right eye rotation parallax permissible value which is a permissible value of a rotation parallax of left and right eyes capable of performing binocular visual performance. In the parallax image changing step, at least one of the left and right parallax images is rotated about a barycenter thereof so that rotational angles of the left and right parallax images change relative to each other. In the measurement value calculating step, the left and right eye rotation parallax permissible value of the subject is calculated based on the predetermine distance and a difference between the rotational angles of the left and right parallax images defined at the detected timing.

In at least one aspect, the binocular visual performance measuring method may further include: a distance changing step of changing the predetermined distance. In this case, the parallax image changing step, the timing detecting step and the measurement value calculating step are executed for each of the changed predetermined distances so that the measurement value of the designated measurement item is obtained for each of the changed predetermined distances.

According to another aspect of the invention, there is provided a binocular visual performance measuring method for measuring binocular visual performance using a stationary 3D video monitor having a display screen on which images for enabling a subject to perform stereoscopic viewing through binocular parallax are displayed. The method includes: a parallax image displaying step of displaying left and right parallax images at a predetermined measurement start position on the display screen when a plurality of types of measurement items of the binocular visual performance are designated; a parallax image changing step of changing one of the left and right parallax images relative to the other of the left and right parallax images in a compositive changing style in which changing patterns respectively corresponding to the plurality of types of designated measurement items are combined; a timing detecting step of detecting a timing when the subject viewing the left and right parallax images from a position a predetermined distance away from the display screen becomes unable to achieve fusion of the left and right parallax images; and a measurement value calculating step of calculating a compositive measurement value of the plurality of types of designated measurement items based on the predetermined distance and a difference between the left and right parallax images defined at the detected timing.

When the compositive binocular visual performance is measured, preparing at least one general-purpose PC and one video monitor and installing the binocular visual performance measuring program onto the general-purpose PC suffices for measurement of the binocular visual performance. Therefore, according to the invention, the introduction cost can be suppressed considerably. Furthermore, the video monitor used for measurement of the binocular visual performance is configured not to require a strong power lens, such as a lens mounted on HMD. Therefore, decrease of the measurement accuracy due to distortion of the image can be suppressed. By appropriately setting the compositive change to be given to the image (movement, rotation, change of magnification), it becomes possible to easily measure the various types of parameters concerning the binocular visual performance.

In at least one aspect, the binocular visual performance measuring method may further include a start position changing step of changing the predetermined measurement start position each time the compositive measurement value of the plurality of types of designated measurement items is calculated. The parallax image changing step, the timing detecting step and the measurement value calculating step are executed in this order while displaying the left and eight parallax images at the changed predetermined measurement position, and the compositive measurement value is obtained for the plurality of types of designated measurement items for each of the changed predetermined measurement start positions.

With this configuration, the measurement value of the designated measurement item can be obtained for each of the different measurement start positions. Therefore, the measurement result can be obtained for each of different visual axis directions.

In at least one aspect, the plurality of types of measurement items include at least two of a relative convergence, a left and right eye vertical divergence permissible value which is a permissible value of a vertical divergence of left and right eyes capable of performing stereoscopic viewing, a first unequal magnification permissible value which is a permissible value of an unequal magnification of left and right eyes capable of performing stereoscopic viewing, a second unequal magnification permissible value which is a permissible value of an unequal magnification defined in a particular direction for left and right eyes capable of performing stereoscopic viewing, a left and right eye rotation parallax permissible value which is a permissible value of a rotation parallax of left and right eyes capable of performing stereoscopic viewing.

In at least one aspect, the plurality of types of designated measurement items are the relative convergence and the left and right eye vertical divergence permissible value. In the parallax image changing step, the left and right parallax images are shifted in a slanting direction on the display screen to approach to or depart from each other, the slanting direction being defined by combining a horizontal direction component and a vertical direction component on the display screen. In the measurement value calculating step, the compositive measurement value of the relative convergence and the left and right eye vertical divergence permissible value is calculated based on the predetermine distance and a position shift amount between the left and right parallax images defined at the detected timing.

In at least one aspect, the plurality of types of designated measurement items further includes one of the first unequal magnification permissible value and the second unequal magnification permissible value. In the parallax image changing step, display magnifications of the left and right parallax images are changed relative to each other while moving the left and right parallax images are in the slanting direction on the display screen to approach to or depart from each other. In the measurement value calculating step, the compositive measurement value of the relative convergence, the left and right eye vertical divergence permissible value, and one of the first unequal magnification permissible value and the second unequal magnification permissible value is calculated based on the predetermine distance and a position shift amount and a rotation angle difference between the left and right parallax images defined at the detected timing.

In at least one aspect, the plurality of types of designated measurement items are the relative convergence and the left and right eye rotation parallax permissible value. In the parallax image changing step, at least one of the left and right parallax images is rotated about a barycenter thereof so that rotational angles of the left and right parallax images change relative to each other while shifting the left and right parallax images in a horizontal direction on the display screen to approach to or depart from each other. In the measurement value calculating step, the compositive measurement value of the relative convergence and the left and right eye rotation parallax permissible value is calculated based on the predetermine distance and a position shift amount and a rotation angle difference between the left and right parallax images defined at the detected timing.

In at least one aspect, the binocular visual performance measuring method further includes a distance changing step of changing the predetermined distance. The parallax image displaying step, the parallax image changing step, the timing detecting step and the measurement value calculating step are executed for each of the changed predetermined distances so that the compositive measurement value of the plurality of designated measurement items is obtained for each of the changed predetermined distances.

According to another aspect of the invention, there is provided a computer readable medium having computer readable instruction stored thereon, which, when executed by a processor of a computer, configures the processor to perform one of the above described binocular visual performance measuring methods.

According to another aspect of the invention, there is provided an eyeglass design method, comprising: measuring binocular visual performance of a subject using one of the above described binocular visual performance measuring methods; and determining optical design values of eyeglass lenses based on a measurement result of the binocular visual performance.

According to another aspect of the invention, there is provided an eyeglass lens manufacturing method, comprising: designing eyeglass lenses using the above described eyeglass design method; and manufacturing the eyeglass lenses according to a design result of the eyeglass lenses.

BRIEF DESCRIPTION OF THE ACCOMPANYING DRAWINGS

FIG. 1 is a block diagram illustrating a configuration of an eyeglass lens manufacturing system for realizing an eyeglass lens manufacturing method according to an embodiment.

FIG. 2 generally illustrates the binocular visual performance measuring system.

DETAILED DESCRIPTION OF THE EMBODIMENTS

Hereinafter, embodiments according to the invention are described with reference to the accompanying drawings.

Figure 1:
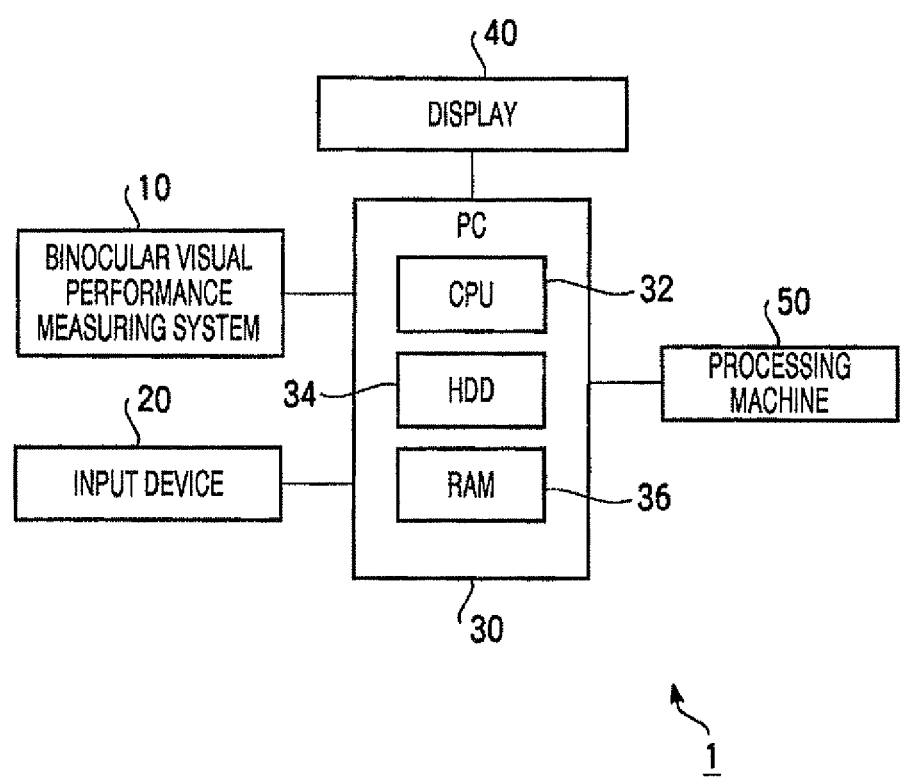

FIG. 1 is a block diagram illustrating a configuration of an eyeglass lens manufacturing system 1 for realizing an eyeglass lens manufacturing method according to the embodiment. The eyeglass lens manufacturing system 1 is installed, for example, in a factory for manufacturing eyeglass lenses. As shown in FIG. 1, the eyeglass lens manufacturing system 1 includes a binocular visual performance measuring system 10, an input device 20 (a keyboard, a mouse or a game pad), a PC (Personal Computer) 30, a display 40 and a processing machine 50. To the PC 30, measured data of the binocular visual performance of a subject measured with the binocular visual performance measuring system 10 and specification data of an eyeglass lens inputted to the input device 20 are inputted. The specification data includes, for example, an optical property and a product type of an eyeglass lens. The optical property of the eyeglass lens includes, for example, a vertex power (a spherical power, a cylindrical power, a cylindrical axis direction, a prismatic power and a prism base setting). The binocular visual performance measuring system 10 and the input device 20 may be installed in an eyeglass store which is located away from the eyeglass lens manufacturing factory. In this case, the measured data obtained by the binocular visual performance measuring system 1 and the specification data inputted to the input device 20 are transmitted to the PC 30 via a computer network.

The PC 30 includes a CPU (central Processing Unit) 32, an HDD (Hard Disk Drive) 34 and a RAM (Random Access Memory) 36. In the HDD 34, a processing control program for controlling the processing machine 50 is installed. The CPU 32 loads the processing control program into the RAM 36. When the processing control program starts up, a GUI (Graphical User Interface) which a user uses to input instructions regarding the design and manufacturing of eyeglass lenses is displayed on the display 40. The processing control program executes optimizing calculation for a surface shape after selecting a semifinished lens based on the specification data and the measured data, and determines optical design values.

An operator sets a selected semifinished lens on the processing machine 50, and inputs instruction for starting the processing by conducting an operation on the GUI. The processing control program reads the determined optical design values and controls the processing machine 50. The processing machine 50 grinds a surface of the semifinished lens in accordance with the processing control program to manufacture an eyeglass lens. An example of a specific design method for an eyeglass lens using the measured data concerning the binocular visual performance is disclosed in WO 2010/090144A1 which was filed by the assignee of this application.

Figure 2:
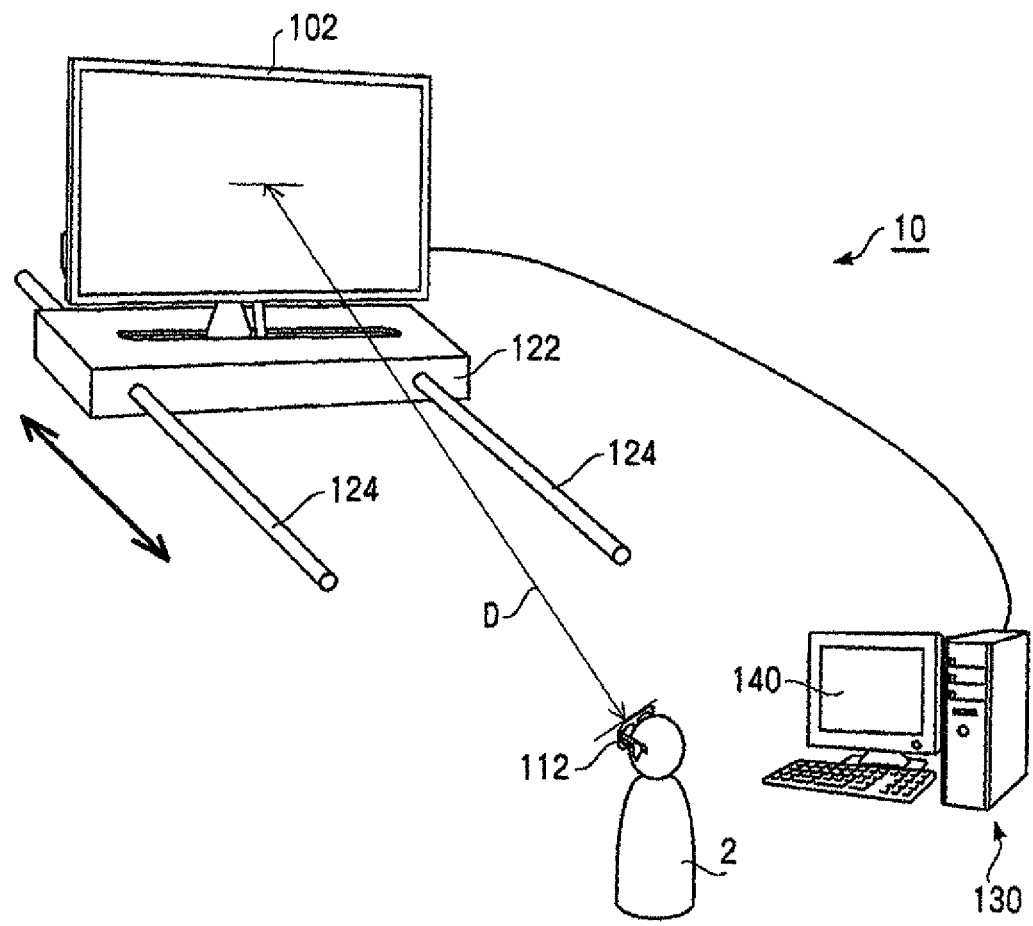
Figure 3:
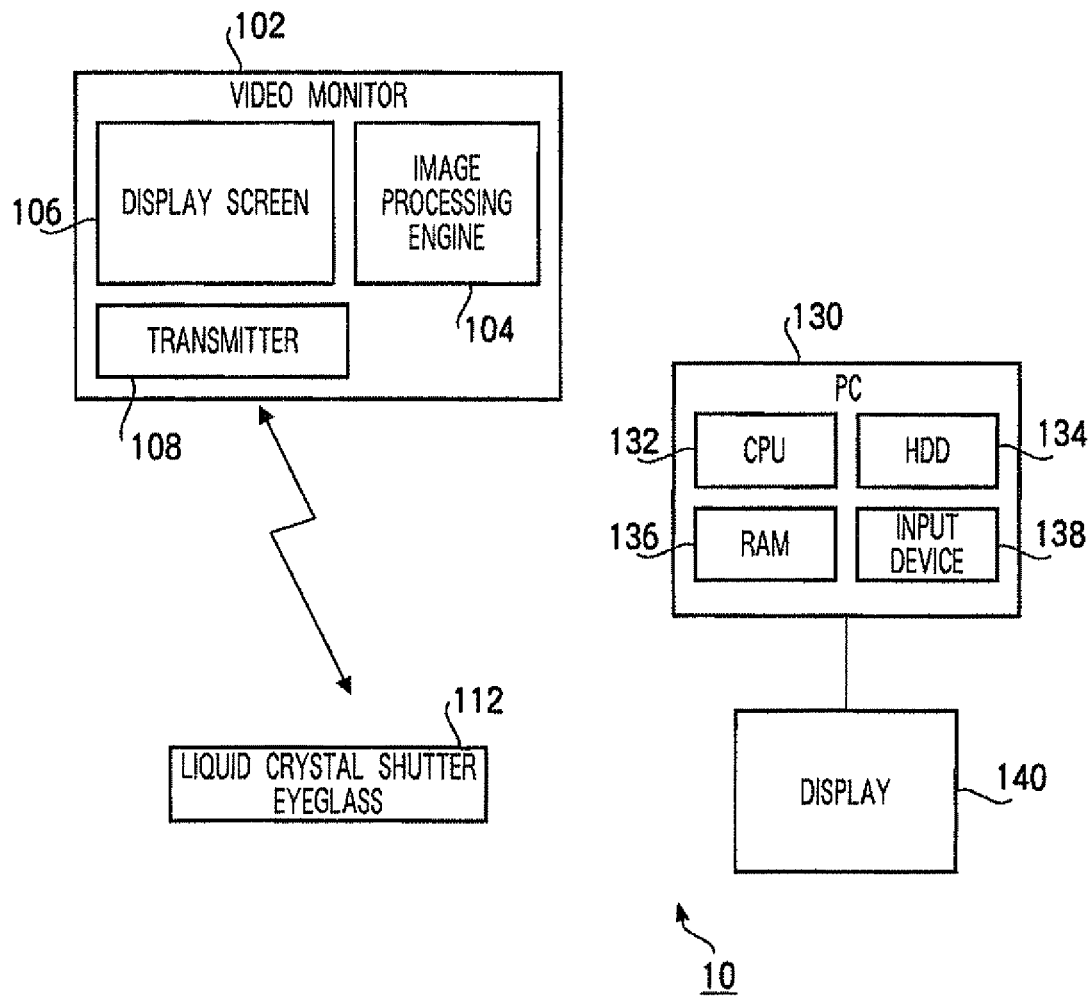
FIG. 3 is a block diagram illustrating a configuration of the binocular visual performance measuring system.

FIG. 2 generally illustrates the binocular visual performance measuring system 10. FIG. 3 is a block diagram illustrating a configuration of the binocular visual performance measuring system 10. In the binocular visual performance measuring method using the binocular visual performance measuring system 10, the binocular visual performance of a subject 2 is measured in regard to a plurality of types of aspects in order to obtain design data (or evaluation data) of eyeglass lenses which cannot be obtained by a prescription focusing on one eye.

As shown in FIGS. 2 and 3, the binocular visual performance measuring system 10 includes a video monitor 102. The video monitor 102 is a stationary video monitor (e.g., a stationary liquid crystal display or a stationary plasma display) which supports displaying of a three dimensional image and enables the subject 2 to perform stereoscopic viewing by utilizing binocular parallax. The video monitor 102 employs a flame sequential scheme. The video monitor 102 generates a right eye image and a left eye image by processing the image data inputted to an image processing engine 104, and displays the images while alternating the left and right eye images at a high speed.

The subject 2 wears a liquid crystal shutter eyeglass 112 and stands at a reference point, and then the subject 2 views a display screen 106 with the subject's head (chin) being fixed. A synchronization signal is transmitted from a transmitter 108 mounted on the video monitor 102 to the liquid crystal shutter eyeglass 112. In accordance with the received synchronization signal, the liquid crystal shutter eyeglass 112 controls the orientation of the liquid crystal in synchronization with the parallax images displayed on the display screen 106, and alternately blocks left and right fields of visions. During a period in which the video monitor 102 and the liquid crystal shutter eyeglass 112 operate in synchronization with each other, the right eye of the subject 2 views only the right eye image and the left eye of the subject 2 views only the left eye image. The subject 2 perceives, as a tree-dimensional object, the parallax images on the video monitor 102 which are converged at non-corresponding points on the retina within the Panum's fusional area.

The displaying format of the three dimensional image on the video monitor 102 utilized by the binocular visual performance measuring system 10 is not limited to the one employing the frame sequential scheme. In place of the frame sequential scheme, an anaglyph scheme where a subject performs the stereoscopic viewing for the parallax images with red and blue filter eyeglasses, or a polarization scheme in which a subject performs the stereoscopic viewing for the parallax images having the polarization conditions being orthogonal to each other by using polarization eyeglasses may be employed. A so-called naked eye scheme, such as a parallax barrier scheme or a lenticular lens scheme may be employed.

The video monitor 102 is placed on a seat 122. The seat 122 is provided to be slidable on rails 124. When the seat 122 slides, the distance (hereafter, referred to as an "observation distance D" for convenience of explanation) between the eyes of the subject 2 and the display screen 106 changes. The operator view the indexes (not shown) added to the side of the rails 124 and recognizes the observation distance D. The observation distance may be obtained as data by detecting a sliding distance of the seat 122 with a sensor (not shown).

To the video monitor 102, a PC 130 is connected. The PC 130 includes a CPU 132, an HDD 134, a RAM 136 and an input device 128 (e.g., a keyboard, a mouse or a game pad). In the HDD 134, the binocular visual performance measuring program for measuring the binocular visual performance has been installed. The CPU 132 loads the binocular visual performance measuring program onto the RAM 136, and starts it. When the binocular visual performance measuring program starts, a GUI for inputting various instructions for the binocular visual performance measurement is displayed on the display 140. The binocular visual performance measuring program generates the data for measurement in accordance with a GUI operation conducted by the operator, and outputs them to the video monitor 102. The data for measurement outputted on the video monitor 102 is processed by the image processing engine 104. The image processing engine 104 processes the inputted data for measurement, generates a measurement screen for measuring the binocular visual performance, and displays the screen on the display screen 106. When all the elements constituting the eyeglass lens manufacturing system 1 are installed in the same place, the PC 30 shown in FIG. 1 and the PC 130 shown in FIG. 2 or 3 may be configured as a single PC. In addition, the input device 20 shown in FIG. 1 and the input device 130 shown in FIG. 2 or 3 may be constituted as a single input device. In addition, the display 40 shown in FIG. 1 and the display 140 shown in FIG. 2 or 3 may be constituted as a single display.

The binocular visual performance measuring program supports various types of measurement items concerning the binocular visual function. As the supported measurement items, the relative convergence, a left and right eye vertical divergence permissible value, a first unequal magnification permissible value, a second unequal magnification permissible value, a left and right eye rotation parallax permissible value) can be cited. In order to start the binocular visual performance measurement, one or more measurement items on the GUI are selected. The operator inputs age and the observation distance D as the measurement conditions. The inputted measurement conditions are stored in the HDD 134. The observation distance D may be calculated by periodically checking the sensor output and may be stored automatically in the HDD 134. In the following, execution of the binocular visual performance measuring program when each of the measurement items is selected is explained.

<Selection of Relative Convergence>

The binocular visual performance measuring program moves to a relative convergence measurement mode for measuring the relative convergence of the subject 2. The relative convergence is a convergence not involving the accommodation. Fundamentally, the convergence (divergence) and the accommodation of an eye work with respect to each other as shown in a known Donders diagram. Therefore, it is not easy to measure the convergence separately from the accommodation. The Donders diagram is described, for example, in a document "written by Shinobu Ishihara and Revised by Shinichi Shikano, "Little pupil science" 17th revised version, Kanehara & Co., Ltd., (1925), p. 50", a document "written by Toyohiko Hatada, "Depth information and a characteristic of a vision," Visual Information Research Group, Apr. 23, 1974, p. 12", and WO 2010/090144A1 filed by the assignee of this application. The straight line of 45 degrees from the origin in the Donders diagram is called the Donders line. The straight line represents the linkage between the accommodation and the convergence, when a subject who does not have a squint nor a heterophoria is viewing an object with naked eyes. On the left and right sides of the Donders line, a Donders curve representing the limit of the convergence (or the divergence) is plotted. The value from a point on the Donders line to the right side Donders curve (the side on which the convergence angle is large) is classified into the negative relative convergence and the value from a point on the Donders line to the left side Donders curve (the side on which the convergence angle is small) is classified into the positive relative convergence.

Figure 4:
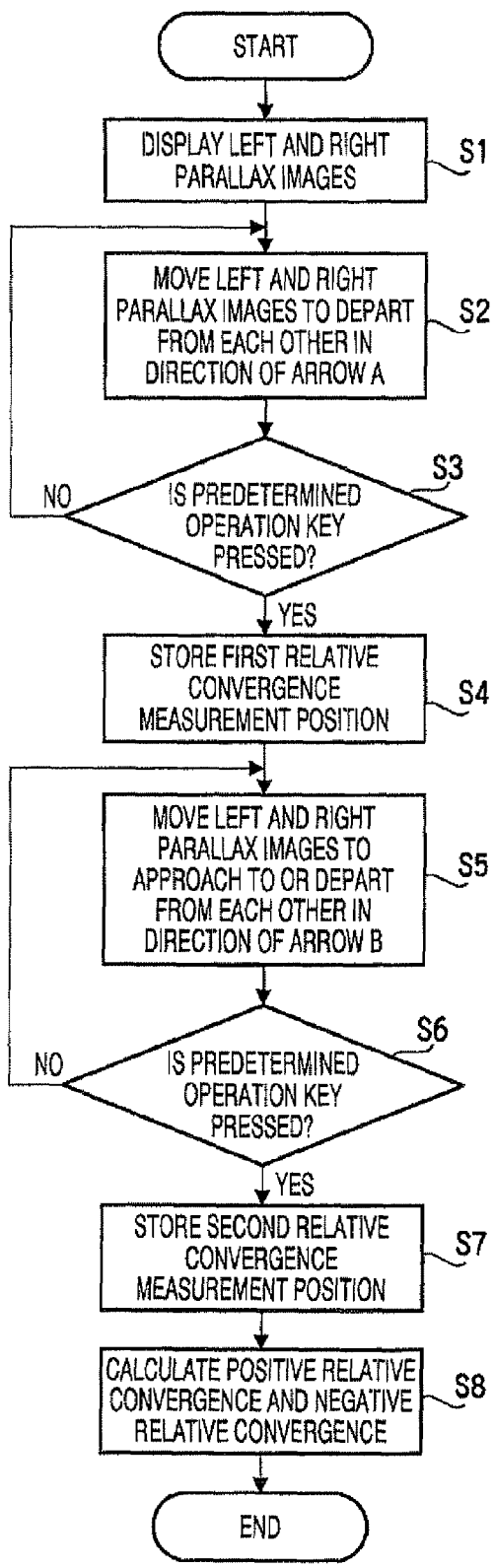
FIG. 4 is a flowchart illustrating a process executed under a relative convergence measurement mode by a binocular visual performance measuring program.
Figure 5A:
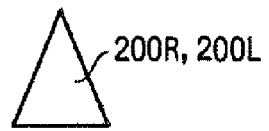
FIGS. 5A to 5C illustrate a screen transition on a display screen during execution of the relative convergence measurement mode.
Figure 5B:
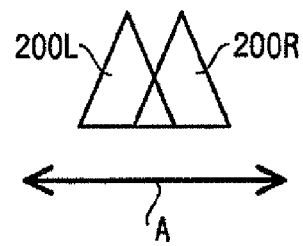
Figure 5C:
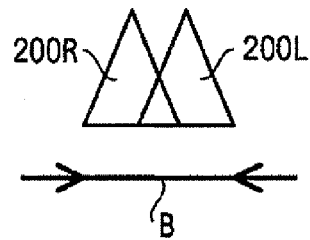

FIG. 4 is a flowchart illustrating a process executed under the relative convergence measurement mode by the binocular visual performance measuring program. FIGS. 5A to 5C illustrate a screen transition on the display screen 106 during execution of the relative convergence measurement mode. In the following explanation and drawings, each step is abbreviated as "S".

When moving to the relative convergence measurement mode, the left eye image 200L and the right eye image 200R are displayed to overlap with each other in a central portion of the display screen 106 as shown in FIG. 5A (see S1 in FIG. 4). The left eye image 200L and the right eye image 200R are the same image (i.e., they have the same size, color and shape). It is preferable that each of the left eye image 200L and the right eye image 200R has a simple geometrical shape so as to enable the subject 2 to concentrate on the measurement. The subject 2 is instructed to press a predetermined operation key of the input device 138 when the subject 2 sees a double image. For example, such an instruction is displayed on the display screen 106. The operator may directly give an instruction to the subject 2. When the measurement items other than the relative convergence are measured, the same instruction may be issued.

In the step of S2 in FIG. 4, as shown in FIG. 5B, the left eye image 200L and the right eye image 200R move in the horizontal direction (in the direction indicated by an arrow A in FIG. 5B) of the display screen 106 to depart from each other. The movement of the images departing from each other is drawn in a continuously changing manner or in incremental steps. The departing movement of the left and right eye images 200L and 200R continues until the predetermined operation key of the input device 138 is pressed (S2 in FIG. 4, S3: NO). When the predetermined operation key is pressed by the subject 2 (S3: YES in FIG. 4), the departing distance (hereafter, referred to as a "first relative convergence measurement position") defined at this moment between the left and right eye images 200L and 200R is stored in the HDD 134 (S4 in FIG. 4). The position of the left eye image 200L and the position of the right eye image 200R may relatively depart from each other. Therefore, one of the left eye image 200L and the right eye image 200R may be fixed during the measurement. The same applies to a left and right eye vertical divergence permissible value measurement mode which is described later.

The time for presentation of the departing images is about 1 second at the maximum, considering the load on the subject 2. The time for representation may be changed by the operator on an as needed basis.

In the process of S5 in FIG. 4, the left eye image 200L and the right eye image 200R move from the first relative convergence measurement position in the horizontal direction (a direction indicated by an arrow B of FIG. 5C which is opposite to the direction of the arrow A) to become close to each other. The left eye image 200L and the right eye image 200R approaches to each other and overlaps with each other, and thereafter successively move in the direction of the arrow B to depart from each other. The movement of the left eye image 200L and the right eye image 200R to be close to each other or to depart from each other, continues until the predetermined operation key of the input device 138 is pressed (S5 in FIG. 4, S6: NO). When the predetermined operation key is pressed by the subject 2 (S6: YES in FIG. 4), the departing distance (hereafter, referred to as a "second relative convergence measurement position") defined at this moment between the left eye image 200L and the right eye image 200R is stored in the HDD 134 S7 in FIG. 4).

In the step of S8 in FIG. 4, a first convergence angle (the divergence limit) is calculated using the first relative convergence measurement position and the observation distance D, and a second convergence angle (the convergence limit) is calculated using the second relative convergence measurement position and the observation distance D. The first convergence angle represents the positive relative convergence corresponding to the accommodation at the observation distance D. The second convergence angle represents the negative relative convergence corresponding to the accommodation at the observation distance D. Therefore, the positive relative convergence and the negative relative convergence can be measured easily and with a high degree of precision while separating the positive relative convergence and the negative relative convergence from the accommodation.

When the positive relative convergence and the negative relative convergence obtained in step S8 in FIG. 4 are applied to Donders diagram, the left and right Donders curves can be predicted. That is, a relationship concerning the cooperation between the convergence and the accommodation of the subject 2 can be obtained. The Donders curve changes depending on the age. Therefore, when the Donders curve is predicted, it is preferable to consider the inputted age as a measurement condition.

When the measurement is performed in the relative convergence measurement mode while changing the observation distance D, the positive relative convergence and the negative relative convergence defined when a different accommodation acts can be measured. As the measurement for the relative convergence at a different observation distance D is repeated, the number of pieces of sample data for predicting the Donders curve increases. Therefore, it becomes possible to obtain the relationship concerning the cooperation between the accommodation and the convergence with a higher degree of precision.

When the departing speed between the left eye image 200L and the right eye image 200R is low, it is assumed that the subject 2 is forced to move the muscle around each eye more strongly than the normal case to achieve the fusion. Since, at this time, the fusional area expands beyond a certain area assumed considering a natural movement of each eye, the measurement accuracy decreases. For this reason, the departing speed is set to be relatively high so that the subject 2 views the left eye image 200L and the right eye image 200R in a relaxed state like the normal case. In the same point of view, the relative change (movement, rotation or scaling) of the left eye image 200L and the right eye image 200R is set to be relatively fast when the other items other than the relative convergence are measured.

The operator is allowed to change the settings regarding the relative speed as appropriate. However, in this case, it is preferable that the settable speed of the relative change falls within a predetermined speed range. For example, the upper limit of the speed of the relative change is determined such that an error caused by the time lag between the timing at which the subject 2 becomes unable to achieve the fusion and the timing at which the predetermined key of the input device 138 is pressed falls within a predetermined range. On the other hand, for example, the lower limit may be set such that representation of the image changes before the fusional area expands beyond the range assumed considering the natural eye ball motion due to the strong activation of the fusion. For example, specific examples of the upper and lower limits are determined by accumulating experimental data.

The departing movement between the left eye image 200L and the right eye image 200R may be performed a plurality of times so as to measure the relative convergence rapidly and with a high degree of precision. For example, at the first measurement (hereafter, referred to as "pre-measurement" for convenience of explanation), the left eye image 200L and the right eye image 200R are moved at a high speed to depart from each other so as to determine the approximate position of the fusion limit. At the second measurement (hereafter, referred to as a "main measurement" for convenience of explanation), the left eye image 200L and the right eye image 200R are moved to depart from each other at a low speed around the approximate position specified by the pre-measurement. Since, in the main measurement, the speed of the departing movement is low, an error caused by the time lag between the timing at which the subject 2 becomes unable to achieve the fusion and the timing at which the predetermined operation key of the input device 138 is pressed can be suppressed, and therefore the measurement accuracy increases. Furthermore, the measuring zone of the main measurement is limited to a region around the approximate position of the fusion limit specified by the pre-measurement. Therefore, the measurement of the relative convergence can be performed rapidly even when both of the pre-measurement and the main measurement are performed. For performing measurements of the other measurement items other than the relative convergence rapidly and with a high degree of precision, both of pre-measurement and main measurement may be performed.

The medium value of the fusional area of the subject 2 is obtained from the positive relative convergence and the negative relative convergence measured in the relative convergence measurement mode. For example, a potential shift (e.g., esotropia and exotropia) of the subject 2 is estimated based on the medium value. Estimation of the medium value can also be made in a similar fashion for the other measurement items other than the relative convergence.

<Selection of "Left and Right Eye Vertical Divergence Permissible Value">

Figure 6:
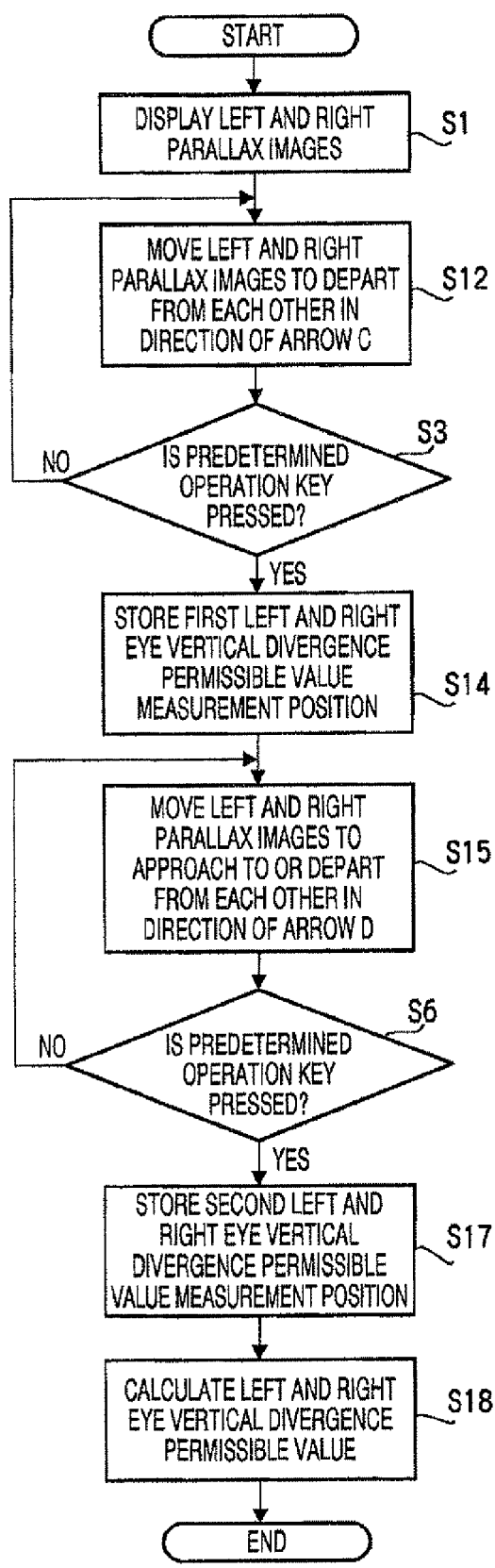
FIG. 6 is a flowchart illustrating a process executed in a left and right eye vertical divergence permissible value measurement mode by the binocular visual performance measuring program.
Figure 7A:
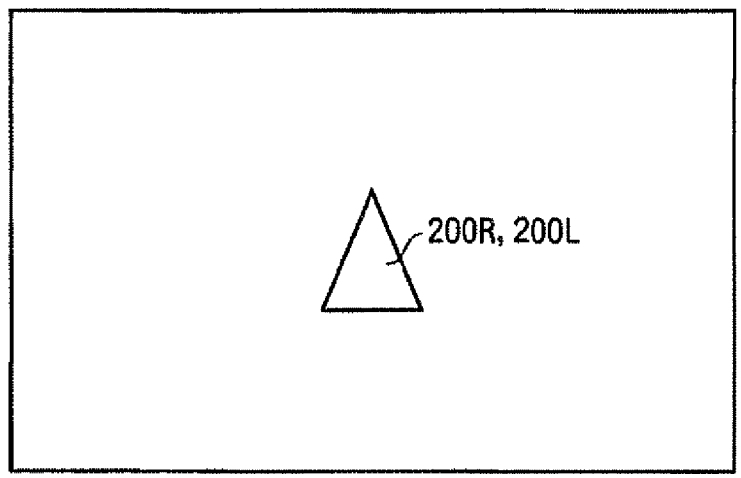
FIGS. 7A to 7C illustrate screen transition of the image displayed on the display screen during execution of the left and right eye vertical divergence permissible value measurement mode.
Figure 7B:
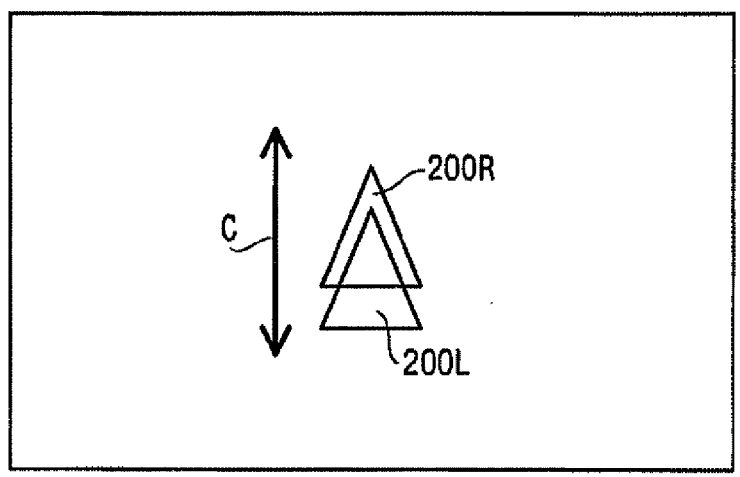
Figure 7C:
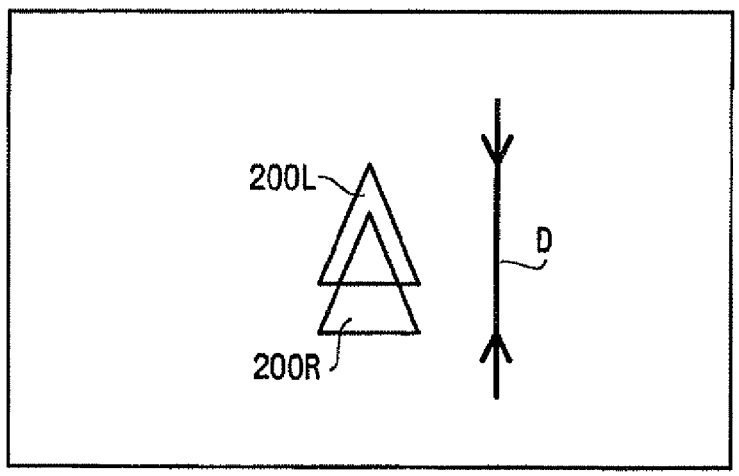

The binocular visual performance measuring program moves to the left and right eye vertical divergence permissible value measurement mode in which the left and right eye vertical divergence permissible value of the subject 2 is measured. The left and right eye vertical divergence permissible value is a permissible value for stereoscopic viewing in regard to the vertical divergence of the left and right eyes. FIG. 6 is a flowchart illustrating a process executed in the left and right eye vertical divergence permissible value measurement mode by the binocular visual performance measuring program. FIGS. 7A to 7C illustrate screen transition of the image displayed on the display screen 106 during execution of the left and right eye vertical divergence permissible value measurement mode. In the flowing explanations and drawings, to element which are substantially the same as those of the above described embodiment, the same reference numbers are assigned and explanations thereof will not be repeated.

When the onscreen representation is presented by moving to the left and right eye vertical divergence permissible value measurement mode (S1 of FIG. 6, FIG. 7A), the left eye image 200L and the right eye image 200R move in the vertical direction (the direction indicated by an arrow C in FIG. 7B) on the display screen 106 to depart from each other as shown in FIG. 7B (S12 of FIG. 6). When the subject 2 presses the predetermined operation key (S3: YES in FIG. 6), the shift amount (hereafter, referred to as a "first left and right eye vertical divergence permissible value measurement position") defined at this moment between the left eye image 200L and the right eye image 200R is stored in the HDD 134 (S14 in FIG. 6).

In step S15 of FIG. 6, the left eye image 200L and the right eye image 200L move in the vertical direction (i.e., a direction indicated by an arrow D in FIG. 7C opposite to the direction of the arrow C) from the first left and right eye vertical divergence permissible value measurement position to approach to each other, and further move to depart from each other as shown in FIG. 7C. When the predetermined key is pressed by the subject 2 (S6: YES in FIG. 6), the shift amount (hereafter, referred to as a "second left and right eye vertical divergence permissible value measurement position") defined at this moment between the left eye image 200L and the right eye image 200R is stored in the HDD 134 (S17 in FIG. 6).

In step S18 of FIG. 6, the left and right eye vertical divergence permissible value and the vertical range in which the fusion for an object can be achieved at the observation distance D are calculated based on the first and second left and right eye vertical divergence permissible value measurement positions and the observation distance D. When the measurement in the left and right eye vertical divergence permissible value measurement mode is performed while changing the observation distance D, a left and right eye vertical divergence permissible value defined when a different accommodation acts (e.g., when a subject views a near position or a far position) is measured.

<Selection of First Unequal Magnification Permissible Value>

A first unequal magnification permissible value represents a permissible value of the unequal magnification of the left and right eyes capable of performing stereoscopic viewing. In general, whether to prepare a proscription for eyeglasses with respect to the unequal magnification is determined in a pattern-like manner in accordance with whether the eyesight difference between the left and right eyes is larger than or equal to 2 diopter. However, since there are individual differences between patients, there is a case where a patient is difficult to achieve the fusion even if the eyesight difference between the left and right eyes is smaller than 2 diopter. In contrast to this fact, there is also a case where a patient is hard to achieve the fusion even if the eyesight difference between the left and right eyes is larger than or equal to 2 diopter. In the following explanations about a first unequal magnification permissible value measurement mode, whether it is possible to achieve the fusion is measured considering the eyesight difference between the left and right eyes. Therefore, by using the results of the first unequal magnification permissible value measurement mode, it becomes possible to give an optimum prescription for the unequal magnification considering the individual differences.

Figure 8:
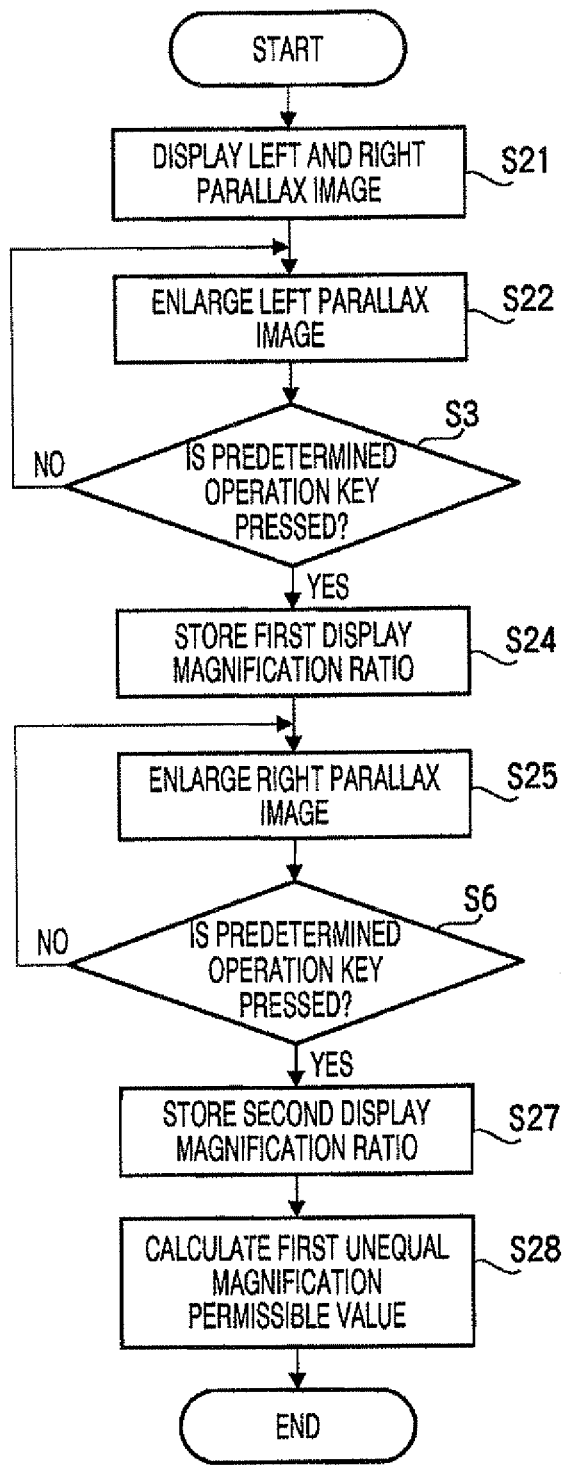
FIG. 8 is a flowchart illustrating a process executed in a first unequal magnification permissible value measurement mode by the binocular visual performance measuring program.
Figure 9A:
FIGS. 9A to 9C illustrate screen transition of the image displayed on the display screen during execution of the first unequal magnification permissible value measurement mode.
Figure 9B:
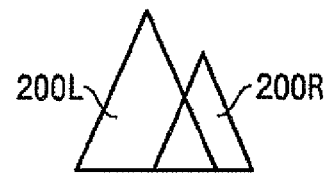
Figure 9C:

The binocular visual performance measuring program moves to the first unequal magnification permissible value measurement mode for measuring the first unequal magnification permissible value of the subject 2. FIG. 8 is a flowchart illustrating a process executed in the first unequal magnification permissible value measurement mode by the binocular visual performance measuring program. FIGS. 9A to 9C illustrate the screen transition of the image displayed on the display screen 106 during execution of the first unequal magnification permissible value measurement mode.

As shown in FIG. 9A, when the program moves to the first unequal magnification permissible value measurement mode, the left eye image 200L and the right eye image 200R are displayed at positions slightly shifted with respect to each other within the fusional area of the subject 2 (S21 in FIG. 8). The displayed positions of the left eye image 200L and the right eye image 200R are determined considering measurement results of the relative convergence and the left and right eye vertical divergence permissible value. When measurement for measuring the relative convergence and the left and right eye vertical divergence permissible value is not performed, the operator makes an adjustment so that the positions of the left eye image and the right eye image 200R fall within the fusional area of the subject 2.

As shown in FIG. 9B, in step S22 in FIG. 8, the left eye image 200L is enlarged with respect to the right eye image 200R. The enlargement rate of the left eye image 200L is fixed in regard to the aspect ratio, and the left eye image 200L is drawn such that the size thereof changes continuously or in incremental steps. The enlargement of the left eye image 200L continues until the predetermined operation key of the input device 138 is pressed (522 in FIG. 8, S3: NO). When the predetermined key is pressed by the subject 2 (53: YES in FIG. 8), the display magnification ratio at this moment (hereafter, referred to as a "first display magnification ratio" for convenience of explanation) between the left eye image 200L and the right eye image 200R is stored in the HDD 134 (S24 in FIG. 8). In the first unequal magnification permissible value measurement mode, the magnifications of the left and right eye images 200L and 200R may be changed relatively with respect to each other. Therefore, the change made to each image may be enlargement or reduction. The same applies to a second unequal magnification permissible value measurement mode which is described later.

As shown in FIG. 9C, in the step of S25 in FIG. 8, the right eye image 200R is enlarged with respect to the left eye image 200L. When the predetermined operation key is pressed by the subject 2 (S6: YES in FIG. 8), the display magnification ratio (hereafter, referred to as a "second display magnification ratio" for convenience of explanation) defined at this moment between the left eye image 200L and the right eye image 200R is stored in the HDD 134 (S27 of FIG. 8).

In step S28 in FIG. 8, the first unequal magnification permissible value at the observation distance D is calculated based on the first and second display magnification ratios and the observation distance D. When the measurement in the first unequal magnification permissible value measurement mode is performed while changing the observation distance D, the first unequal magnification permissible value defined when a different accommodation acts (e.g., when a subject views a near position or a far position) is measured.

<Selection of Second Unequal Magnification Permissible Value>

Figure 10:
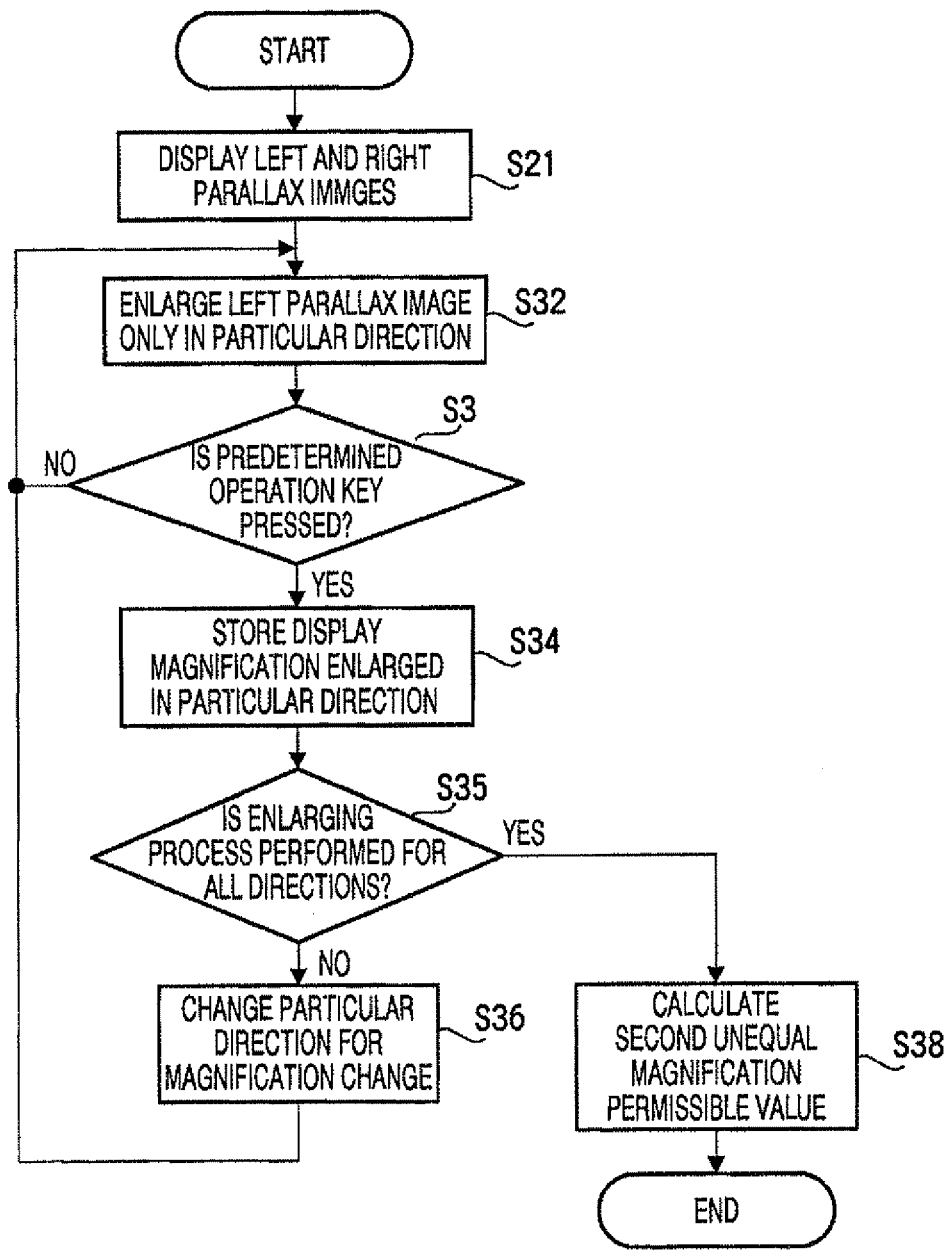
FIG. 10 is a flowchart illustrating a process executed in a second unequal magnification permissible value measurement mode by the binocular visual performance measuring program.
Figure 11A:
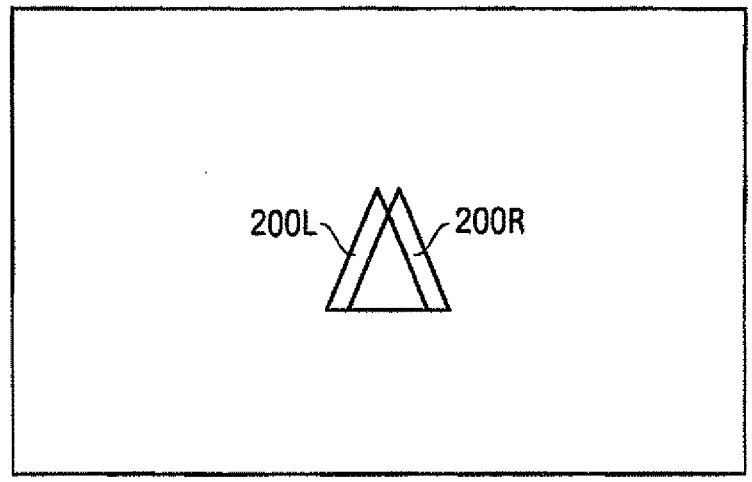
FIGS. 11A to 11C illustrate transition of the image displayed on the display screen during execution of the second unequal magnification permissible value measurement mode.
Figure 11B:
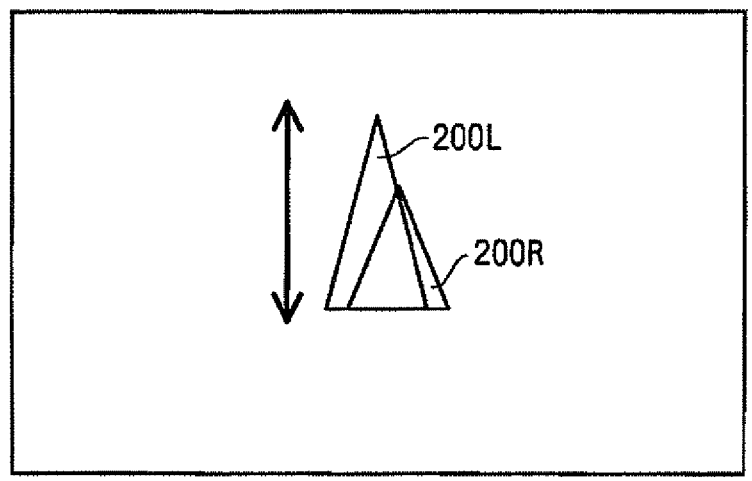
Figure 11C:
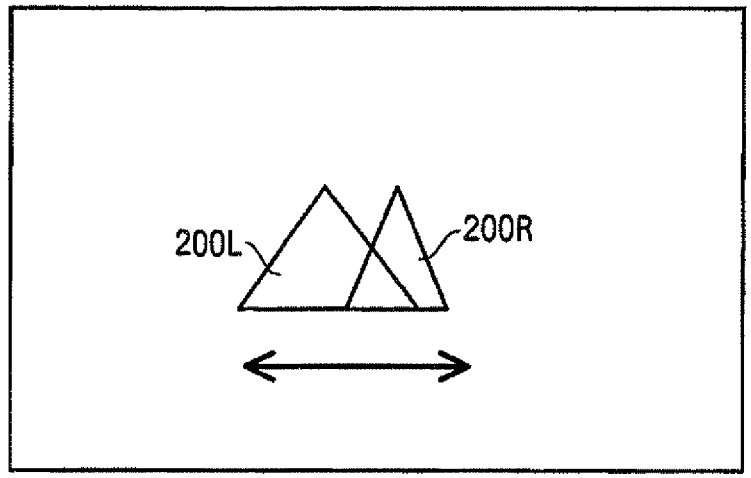

The binocular visual performance measuring program moves to a second unequal magnification permissible value measurement mode in which a second unequal magnification permissible value is measured. The second unequal magnification permissible value is a permissible value of the unequal magnification limited to a particular direction of the left and right eyes capable of performing stereoscopic viewing. FIG. 10 is a flowchart illustrating a process executed in the second unequal magnification permissible value measurement mode by the binocular visual performance measuring program. FIGS. 11A to 11C illustrate transition of the image displayed on the display screen 106 during execution of the second unequal magnification permissible value measurement mode.

When the program moves to the second unequal magnification permissible value measurement mode and onscreen representation is made (S21 of FIG. 10, FIG. 11A), the left eye image 200L is enlarged in a particular direction with respect to the right eye image 200R (S32 in FIG. 10). In the image example in FIG. 11B, the displaying magnification of the left eye image 200L is enlarged only in the vertical direction. The enlargement of the left eye image 200L is drawn such that the size thereof changes continuously or in incremental steps. The enlargement of the left eye image 200L continues until the predetermined operation key of the input device 138 is pressed (S32, S3: NO in FIG. 10). When the predetermined operation key is pressed by the subject 2 (S3: YES in FIG. 10), the display magnification ratio (hereafter, referred to as a "first particular direction magnification ratio" for convenience of explanation) defined at this moment between the left eye image 200L and the right eye image 200R is stored in the HDD 134 (S34 in FIG. 10).

In step S35 in FIG. 10, it is judged whether the enlargement of the left eye image 200L in all the particular directions of magnification change targets. In this embodiment, the directions of the magnification change targets are two directions including the vertical direction and the horizontal direction. Therefore, the direction of the magnification change target is changed to the horizontal direction (S35: N0, S36 in FIG. 10). Then, as shown in FIG. 11C, the left eye image 200L is enlarged in the horizontal direction with respect to the right eye image 200R. When the predetermined operation key is pressed by the subject 2 (S3: YES in FIG. 10), the display magnification (hereafter, referred to as a "second particular direction magnification ratio" for convenience of explanation) defined at this moment between the left eye image 200L and the right eye image 200R is stored in the HDD 134 (S34 in FIG. 10).

In step S38 in FIG. 10, the second unequal magnification permissible value at the observation distance D is calculated based on the first and second particular direction magnification ratios and the observation distance D. When the measurement in the second unequal magnification permissible value measurement mode is performed while changing the observation distance D, the second unequal magnification permissible value defined when a different accommodation acts (e.g., when a subject views a near position or a far position) is measured. The target directions of magnification change are not limited to the above described two directions, and may include another direction.

<Selection of a "Left and Right Eye Rotation Parallax Permissible Value">

Fusional rotation may be caused when the visual axes are not parallel with each other (e.g., in the case of convergence). For far vision, rotation of an eyeball is based on Listing's Law. The Listing's Law is a law which defines the posture defined when an eyeball points to a certain direction in space. The posture of an eyeball represents the direction of the eyeball in the vertical direction and in the horizontal direction. If the posture of the eyeball is not defined, upward, downward, left and right directions of a retinal image are not defined. The posture of the eyeball is not defined uniquely by only the visual axis direction (i.e., an optical axis direction of the eyeball). The posture of the eyeball can take all the directions defined in regard to rotation about an axis (visual axis) even when the visual axis is defined.

Listing's Law defines the posture of an eyeball pointing to a given visual axis direction to a point at infinity. In "Handbook of Visual Information Processing" p. 405, it is described that it can be regarded that any rotation of a single eye is caused about an axis in a plane (Listing's plane).

Figure 12:
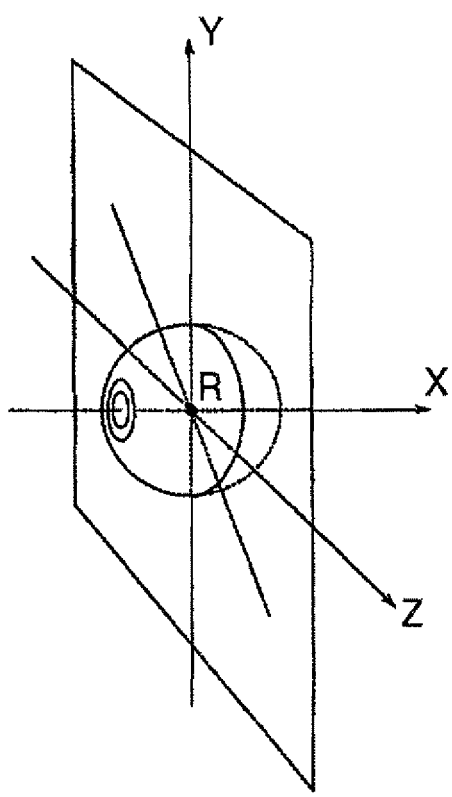
FIG. 12 is an explanatory illustration for explaining the Listing's law.

The above described explanation about the Listing's law is explained with reference to a coordinate shown in FIG. 12. The coordinate shown in FIG. 12 is a coordinate having an origin, a point R, equal to a rotation center of an eyeball, and a direction entering an eye from the front face (horizontal front side) is defined as X axis direction, a direction perpendicular to the X axis direction is defined as Y direction, and a horizontal direction perpendicular to the X axis direction is defined as Z axis direction. Y-Z plane is the Listing's plane.

The posture after rotation of an eyeball to a given direction is equal to rotation about an axis equal to a line which includes the point R and in the Listing's plane. In FIG. 12, an example of such a line serving as the rotation axis is illustrated between Y axis and Z axis (on Y-Z plane). The rotation axis is perpendicular to each of the primary position of eye (X axis) and the visual axis after rotation. Let us consider the case where an eyeball is rotated to a directional vector (L, M, N) which is not shown. In this case, the vector in X, Y and Z axis directions of an eyeball coordinate after rotation is calculated by the following expression (1):

$$x = Li + Mj + Nk$$
$$y = -Mi + \left(1 - \frac{M^2}{1+L}\right)j - \frac{MN}{1+L}k$$
$$z = -Ni - \frac{MN}{1+L}j + \left(1 - \frac{N^2}{1+L}\right)k$$
(1)

Listing's Law is considered to be appropriate in regard to a case where a single eye defines a posture with respect to an object at an infinite distance. When a subject bends the subject's body while viewing an object at an infinite distance, the left and right eyes have the same posture and the same rotation. On the other hand, when a subject views an object not at an infinite distance, the left eye and the right eye may have different postures.

Figure 13:
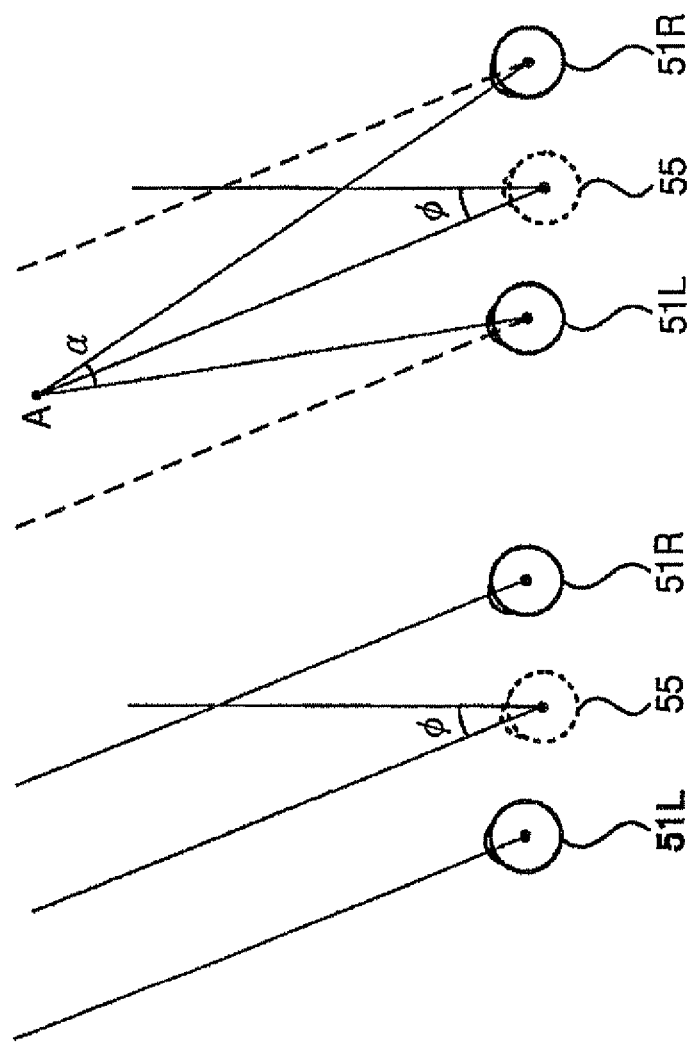
FIGS. 13A and 13B are explanatory illustrations for explaining the visual direction of left and right eyes during the binocular viewing.

FIGS. 13A and 13B are explanatory illustrations for explaining the visual direction of the left and right eyes during the binocular viewing. In each of FIGS. 13A and 13B, a dashed line represents a virtual eyeball 55 arranged at an intermediate position between the left eyeball 51L and the right eyeball 51R. As shown in FIG. 13A, when an object at an infinite distance is viewed, both of the eyeball 51L and the eyeball 51R point to the same visual direction. Since each of the left and right eyeballs follows the Listing's Law, the postures after the rotation are also the same. In this case, there is no difference between the retinal images between the left and right eyes.

On the other hand, as shown in FIG. 13B, when an object (point A) at a finite distance is viewed, the convergence is required. In this case, since the visual axes of the left and right eyeballs 51L and 51R are different from each other, the rotation amounts of the left and right eyeballs are different from each other. In FIG. 13B, the point A is on the leftward front side. Therefore, the rotation amount of the eyeball 51R is larger than the rotation amount of the eyeball 51L.

Regarding the eyeball rotation based on the Listing's Law, the posture of the eyeball after rotation, i.e., each of the directional vectors in the Y axis and Z axis directions after rotation, depends on the visual direction vector shown in the expression (1). When the visual direction vectors of the left and right eyes are different from each other, the directional vectors of the Y and Z axes after rotation are different between the left and right eyes. Therefore, the rotational shift occurs in the retinal images. In order to cancel the rotational shift of the retinal images, rotation about the visual axis is required for both of the left and right eyes. Such rotation about the visual axis is the fusional rotation.

Figure 14:
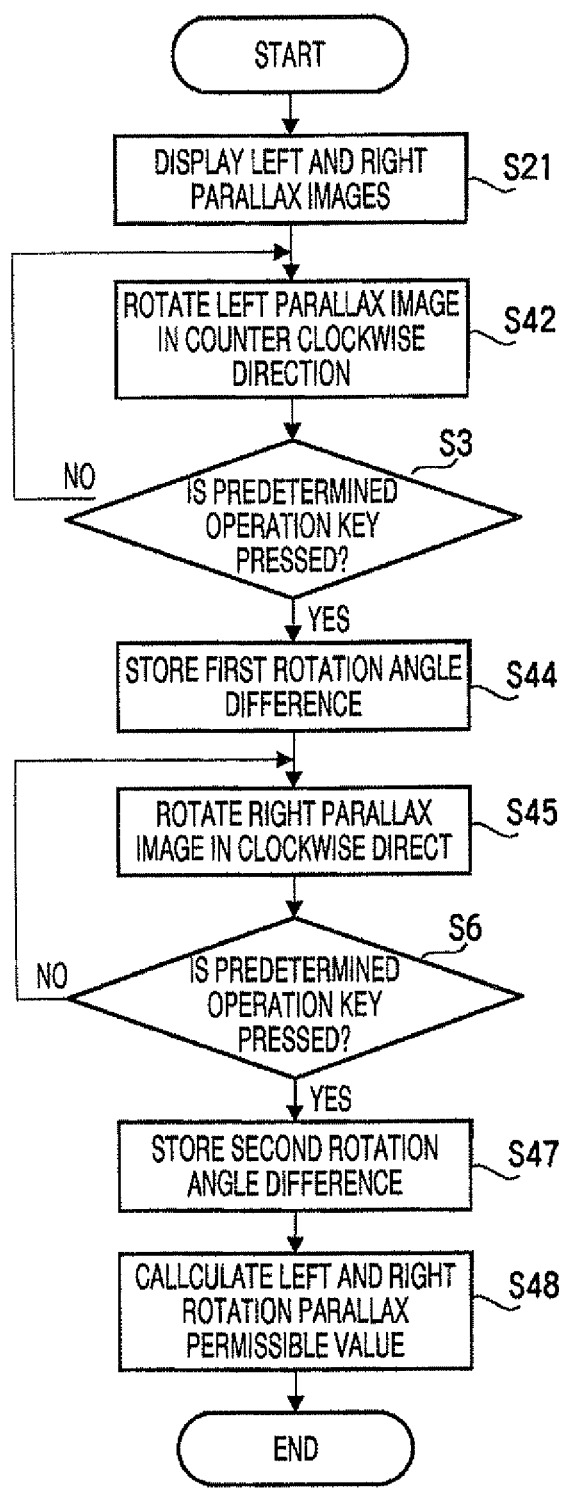
FIG. 14 is a flowchart illustrating a process executed in a left and right eye rotation parallax permissible value measurement mode by the binocular visual performance measuring program.
Figure 15A:
FIGS. 15A to 15C illustrate transition of the image displayed on the display screen 106 during execution of the left and right eye rotation parallax permissible value measurement mode.
Figure 15B:
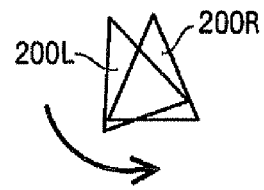
Figure 15C:
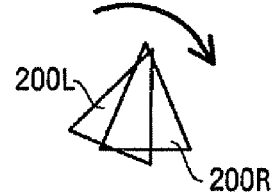

When the fusional rotation occurs, the rotational parallax is caused between the left and right eyes. In the binocular visual performance measuring program, the left and right eye rotation parallax permissible value which is a permissible value of the rotational parallax of the left and right eyes capable of performing the stereoscopic viewing can be measured. When the measurement item "left and right eye rotation parallax permissible value" is selected, the program moves to the left and right eye rotation parallax permissible value measurement mode where the left and right eye rotation parallax permissible value of the subject 2 is measured. FIG. 14 is a flowchart illustrating a process executed in the left and right eye rotation parallax permissible value measurement mode by the binocular visual performance measuring program. FIGS. 15A to 15C illustrate transition of the image displayed on the display screen 106 during execution of the left and right eye rotation parallax permissible value measurement mode. When the program moves to the left and right eye rotation parallax permissible value measurement mode and images are displayed (S21 of FIG. 14, FIG. 15A), the left eye image 200L rotates counterclockwise as shown in FIG. 15B (S42 of FIG. 14). The rotation of the left eye image 200L is drawn in a continuously changing manner or in incremental steps. The rotation of the left eye image 200L continues until the predetermined operation key of the input device 138 is pressed by the subject 2 (S42, S3: NO in FIG. 14). When the predetermined operation key is pressed by the subject 2 (S3: YES in FIG. 14), the rotational angle difference defined at this moment between the left eye image 200L and the right eye image 200R (hereafter, referred to as a "first rotational angle difference" for convenience of explanation) is stored in the HDD 134 (S44 in FIG. 14). The rotation center of each image is defined at the barycenter of the image. In the left and right eye rotation parallax permissible value measurement mode, the rotational angle difference between the left and right eye images 200L and 200R may change relative to each other. Therefore, during the measurement, the left and right eye images 200L and 200R may be rotated simultaneously at different speeds or in different directions.

In step S45 in FIG. 14, as shown in FIG. 15C, the left eye image 200L rotates clockwise. When the predetermined operation key is pressed by the subject 2 (S6: YES in FIG. 14), the rotational angle difference (hereafter, referred to as a "second rotational angle difference" for convenience of explanation) defined at this moment between the left and right eye images 200L and 200R is stored in the HDD 134 (S47 in FIG. 14).

In step S48 in FIG. 14, the left and right eye rotation parallax permissible value at the observation distance D is calculated based on the first and second rotational angle differences and the observation distance D. When the measurement in the left and right eye rotation parallax permissible value measurement mode is performed while changing the observation distance D, the left and right eye rotation parallax permissible value defined when a different accommodation acts (e.g., when a subject views a near position or a far position) is measured. By measuring the left and right eye rotation parallax permissible value for each of the different observation distances, it becomes possible to suitably cure the astigmatism by prescribing different astigmatic axes between a near vision part and a far vision part of a progressive-power spectacle lens.

<Other Measurement>

The stereoscopic viewing can also be measured with the binocular visual performance measuring system 10. In the measurement for the stereoscopic viewing, two types of parallax images having different shapes are displayed on the display screen 106, for example. In order to allow the subject 2 to concentrate on the measurement, the image may have a geometric shape, such as a circle or a triangle. In this embodiment, the two types of parallax images are a circle image and a triangle image. The circle image has the larger degree of parallax than the triangle image. Therefore, the subject 2 recognizes that the circle image shows up on the front side and the triangle image shows up on the deep side. Next, the parallax of at least one of the circle image and the triangle image is changed continuously or in incremental steps. The subject 2 presses the predetermined operation key of the input device 138, for example, when the subject 2 feels that each of the circle image and the triangle image does not have depth or when the double image appears. In the HDD 134, the parallax of images defined when the predetermined operation key is pressed is stored. The CPU 132 calculates the limit within which the subject 2 is able to perform stereoscopic viewing based on the stored parallax of images and the observation distance D.

<Compositive Measurement for Measurement Items>

In each of the above described various types of measurement modes, one measurement item is measured. In another measurement mode, a compositive measurement in which a plurality of measurement items (e.g., at least two of the relative convergence, the left and right eye vertical divergence permissible value, the first unequal magnification permissible value, the second unequal magnification permissible value, and the left and right eye rotation parallax permissible value) are measured simultaneously may be performed. In particular, when a plurality of measurement items which are closely related to each other are measured simultaneously, a possibility arises that a measurement result that cannot be recognized by a result of measurement of a single measurement item can be obtained. The operator is able to select measurement items to be measured simultaneously. Some combinations of measurement items may be prepared in advance. In the following, three examples of the compositive measurement modes are explained.

<Compositive Measurement of Relative Convergence and Left and Right Eye Vertical Divergence Permissible Value>

For example, the relative convergence and the left and right eye vertical divergence permissible value have strong mutual interaction. Therefore, in a first compositive measurement mode, the relative convergence and the left and right eye vertical divergence permissible value are measured simultaneously by moving, continuously on in increment steps, at least one of the left eye image 200L and the right eye image 200R in a slanting direction on the screen. The slanting direction means any directions other than the horizontal direction and the vertical direction, and includes a horizontal direction component and a vertical direction component on the screen. That is, change of representation (hereafter, referred to as "a compositive change") obtained by combining the changing patterns (movement in the horizontal direction and the vertical direction on the screen) of the relative convergence measurement mode and the left and right eye vertical divergence permissible value measurement mode is given to the left and right eye images 200L and 200R. The angle of the slanting direction on the screen may be set by the operator or may be determined in advance by the binocular visual performance measuring program.

Figure 16:
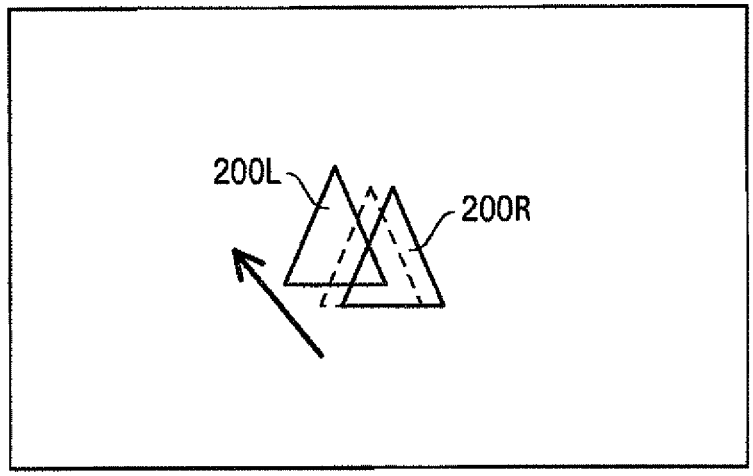
FIG. 16 illustrates an example of an image in a first compositive measurement mode.

FIG. 16 is an example of display of the image in the first compositive measurement mode. Since a flowchart of the first compositive measurement mode is equal to, for example, the flowchart of the relative convergence measurement mode, explanation thereof will not be repeated. As shown in the example of FIG. 16, the left eye image 200L moves in the slanting direction on the screen from a position indicated by a dashed line. The movement in the slanting direction on the screen continues until the predetermined operation key of the input device 138 is pressed. When the predetermined operation key is pressed by the subject 2, the departing amount defined at this moment between the left and right eye images 200L and 200R is stored in the HDD 134. In a sequence of measurement, a plurality of pieces of measurement data of the departing amounts may be measured while moving the left eye image 200L or the right eye image 200R in different slanting directions. Based on each departing amount and the observation distance D stored in the HDD 134, the compositive measurement result of the relative convergence and the left and right eye vertical divergence permissible value defined at the observation distance D is calculated. When the measurement in the first compositive measurement mode is performed while changing the observation distance D, a compositive measurement result defined when a different accommodation acts (e.g., when a subject views a near position or a far position) can be obtained.

<Compositive Measurement of Relative Convergence and Left and Right Eye Vertical Divergence Permissible Value and Second Unequal Magnification Permissible Value (or First Unequal Magnification Permissible Value>

For example, the relative convergence, the vertical divergence and the unequal magnification of the left and right eyes have strong mutual interaction. Therefore, in a second compositive measurement mode, at least one of the left and right eye images 200L and 200R is moved in a slanting direction on the screen continuously or in incremental steps and is enlarged or reduced. When the enlargement or the reduction of the image is limited to a particular direction, the measurement is performed for the second unequal magnification permissible value. When the enlargement or the reduction of the image is performed in a fixed aspect ratio, the measurement is performed for the first unequal magnification permissible value. The compositive change obtained by combining the changing patterns (movement in the horizontal direction and the vertical direction on the screen and change of display magnification) of the relative convergence measurement mode, the left and right eye vertical divergence permissible value measurement mode and the second unequal magnification permissible value measurement mode (or the second unequal magnification permissible value measurement mode) is given to the left and right eye images 200L and 200R. Settings regarding how the changing patterns are combined may be set by the operator or may be determined in advance by the binocular visual performance measuring program.

Figure 17:
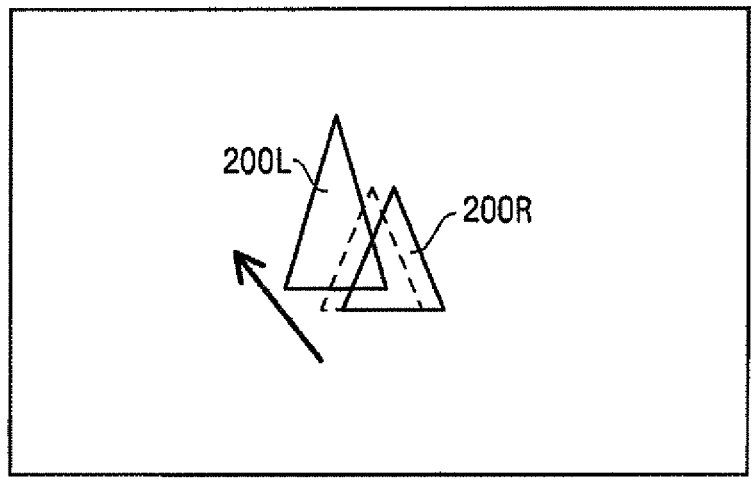
FIG. 17 illustrates an example of an image in a second compositive measurement mode.

FIG. 17 is an example of display of the image in the second compositive measurement mode. Since a flowchart of the second compositive measurement mode is equal to, for example, the flowchart of the relative convergence measurement mode, explanation thereof will not be repeated. As shown in the example of FIG. 17, the left eye image 200L moves in a slanting direction on the screen from a position indicated by a dashed line and is enlarged only in the vertical direction on the screen. The movement in the slanting direction and the enlargement of the left eye image 200L on the screen continues until the predetermined operation key of the input device 138 is pressed. When the predetermined operation key is pressed by the subject 2, the departing amount and the display magnification ratio in the vertical direction defined at this moment (hereafter, referred to as an "image change status" for convenience of explanation) between the left and right eye images 200L and 200R is stored in the HDD 134. In a sequence of measurement, a plurality of pieces of measurement data of the image change status may be measured while performing movement and enlargement of the left eye image 200L or the right eye image 200R in different patterns. Based on each image change status and the observation distance D stored in the HDD 134, the compositive measurement result of the relative convergence, the left and right eye vertical divergence permissible value and the second unequal magnification permissible value (or the first unequal magnification permissible value) defined at the observation distance D is calculated. When the measurement in the second compositive measurement mode is performed while changing the observation distance D, compositive measurement result defined when a different accommodation acts (e.g., when a subject views a near position or a far position) can be obtained.

<Compositive Measurement of Relative Convergence and Left and Right Eye Rotation Parallax Permissible Value>

As described above, the fusional rotation occurs in conjunction with the convergence. Therefore, in a third compositive measurement mode, at least one of the left and right eye images 200L and 200R is moved and rotated in a clockwise direction or in a counterclockwise direction continuously or in increment steps. That is, compositive change obtained by combining the changing patterns (movement in the horizontal direction on the screen and rotation with respect to the barycenter of the image) of the relative convergence measurement mode and the left and right eye rotation parallax permissible value measurement mode is given to the left and right eye images 200L and 200R. Settings regarding how the changing patterns are combined may be set by the operator or may be determined in advance by the binocular visual performance measuring program.

Figure 18:
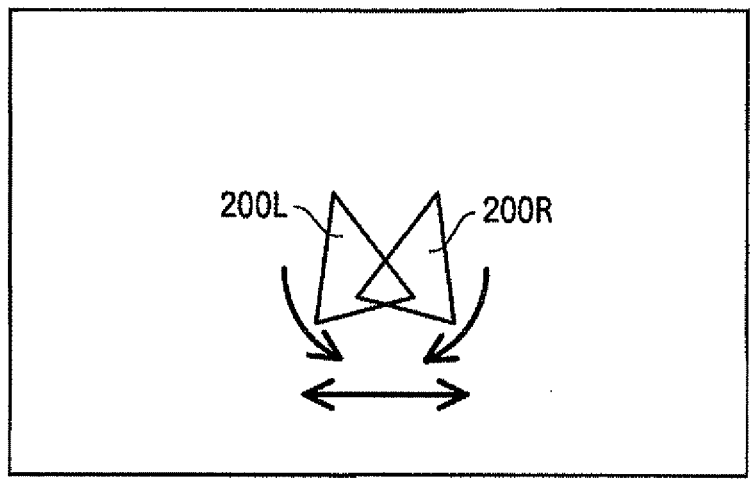
FIG. 18 illustrates an example of an image in a third compositive measurement mode.

FIG. 18 is an example of display of the image in the third compositive measurement mode. Since a flowchart of the third compositive measurement mode is equal to, for example, the flowchart of the relative convergence measurement mode, explanation thereof will not be repeated. As shown in the example of FIG. 18, the left and right eye images 200L and 200R depart from each other by moving in the horizontal direction on the screen and rotate in the counterclockwise direction and in the clockwise direction, respectively. The movement and rotation of the left and right eye images 200L and 200R continue until the predetermined operation key of the input device 138 is pressed. When the predetermined operation key is pressed by the subject 2, the departing amount and the rotation angle difference defined at this moment between the left and right eye images 200L and 200R is stored in the HDD 134. In a sequence of measurement, a plurality of pieces of data of the departing amount and the rotation angle difference may be measured while performing repeatedly movement and rotation of the left and right eye images 200L and 200R in different patterns. Based on the departing amounts, the rotation angle difference and the observation distance D stored in the HDD 134, the compositive measurement result of the relative convergence and the left and right eye rotation parallax permissible value defined at the observation distance D is calculated. When the measurement in the third compositive measurement mode is performed while changing the observation distance D, a compositive measurement result defined when a different accommodation acts (e.g., when a subject views a near position or a far position) can be obtained.

According to the above described compositive measurement, it becomes possible to suitably measure a plurality of types of binocular visual performance that act in combination.

<Measurement in Consideration of Lateral Gaze>

Figure 19:
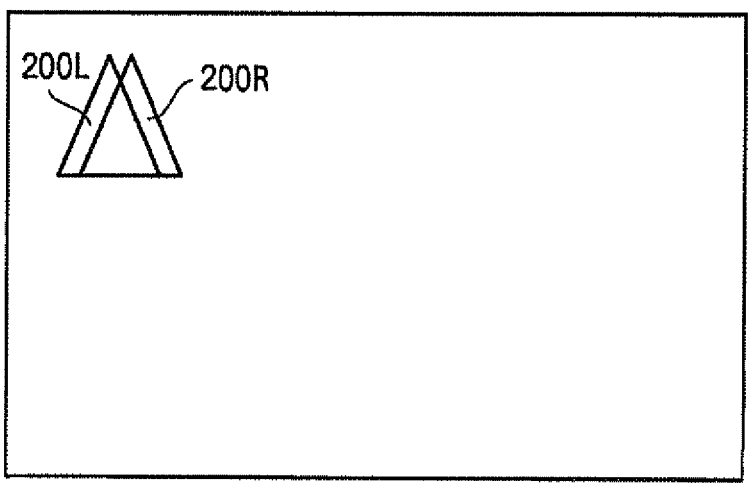
FIG. 19 illustrates an example of a measurement mode in consideration of lateral gaze.

In the above described each measurement mode, the left and right eye images 200L and 200R are displayed in the central portion of the display screen 106. Therefore, the measurement only provides the measurement result in a condition where the subject 2 faces the front. For this reason, after the measurement in which the subject 2 faces the front is finished, the display positions of the left and right eye images 200L and 200R are moved to the peripheral portion (the upper left corner of the screen) of the display screen 106 as shown, for example, in FIG. 19. Since the subject 2 is instructed to fix his/her head, the subject 2 inevitably views the left and eight eye images 200L and 200R by lateral gaze. When the measurement is performed in this condition, the measurement result where the subject 2 in the state of lateral gaze can be obtained. Furthermore, when the measurement is performed while moving the left and right eye images 200L and 200R to different positions in the peripheral portion on the screen (e.g., the center of the upper edge of the screen, the upper right corner of the screen, the center of the right edge of the screen, the lower right corner of the screen and etc.), measurement results in conditions of various types of lateral gaze directions can be obtained. Therefore, by designing eyeglass lenses additionally considering such measurement results, it becomes possible to provide more suitable prescriptions.

The foregoing is the explanation about the embodiment. When the binocular visual performance measuring method according to the present invention (measurement of the binocular visual performance or measurement of the compositive binocular performance) is used, preparing at least one general-purpose PC and one video monitor and installing the binocular visual performance measuring program onto the general-purpose PC suffices for measurement of the binocular visual performance. Therefore, according to the invention, the introduction cost can be suppressed considerably. Furthermore, the video monitor used for measurement of the binocular visual performance is configured not to require a strong power lens, such as a lens mounted on HMD. Therefore, decrease of the measurement accuracy due to distortion of the image can be suppressed. By appropriately setting change (or the compositive change) to be given to the image (movement, rotation, change of magnification), it becomes possible to easily measure the various types of parameters concerning the binocular visual performance.

Although the present invention has been described in considerable detail with reference to certain preferred embodiments thereof, other embodiments are possible. For example, although, in the above described embodiment, the rate of each of movement, rotation and magnification change of each of the left and right eye images 200L and 200R is constant, in another embodiment the rate of each of movement, rotation and magnification change of at least one of the left and right eye images 200L and 200R may be varied at an accelerating pace.

The speed of the relative movement of the left and right parallax images may be settable. The relative movement may be a constant speed or an accelerating pace. It is preferable that the speed of the relative movement falls within a predetermined range. The upper limit speed of the relative movement may be set to such a value that an error caused by a time lag between a timing when the subject becomes unable to achieve the fusion and a timing when the subject conduct the predetermined user operation with respect to the input device falls within a predetermined permissible value. The lower limit speed of the relative movement may be set to such a value that the displayed image changes before the fusional area expands, due to the strong effect by the fusion, beyond an area assumed with respect to a natural eye ball action. The upper and lower limit speeds may be determined by making repeated experiments.

This application claims priority of Japanese Patent Applications No. P2010-243499, filed on Oct. 29, 2010, and No. P2010-243500, filed on Oct. 29, 2010. The entire subject matter of the applications is incorporated herein by reference.

What is claimed is:

1. A binocular visual performance measuring method for measuring binocular visual performance using a stationary 3D video monitor having a display screen on which images for enabling a subject to perform stereoscopic viewing through binocular parallax are displayed, the method comprising:
a parallax image displaying step of displaying left and right parallax images at a predetermined measurement start position on the display screen when a plurality of types of closely related measurement items of the binocular visual performance are designated;
a parallax image changing step of changing one of the left and right parallax images relative to the other of the left and right parallax images;
a timing detecting step of detecting a timing when the subject viewing the left and right parallax images from a position a predetermined distance away from the display screen becomes unable to achieve fusion of the left and right parallax images; and
a measurement value calculating step of calculating corresponding measurement data of the plurality of types of closely related measurement items respectively, wherein:
in the parallax image changing step, one of the left and right parallax images is changed in a composite changing style in which changing patterns respectively corresponding to the plurality of types of closely related measurement items are combined;
in the measurement value calculating step, the corresponding measurement data is calculated based on the predetermined distance and a difference between the left and right parallax images defined at the detected timing; and
the corresponding measurement data represents measurement values of the plurality of types of closely related measurement items.

2. The binocular visual performance measuring method according to claim 1,
further comprising:
a start position changing step of changing the predetermined measurement start position each time the corresponding measurement data of the plurality of types of closely related measurement items is calculated,
wherein the parallax image changing step, the timing detecting step and the measurement value calculating step are executed in this order while displaying the left and eight parallax images at the changed predetermined measurement position, and the corresponding measurement data is obtained for the plurality of types of closely related measurement items for each of the changed predetermined measurement start positions.

3. The binocular visual performance measuring method according to claim 1,
wherein the plurality of types of closely related measurement items include at least two of a relative convergence, a left and right eye vertical divergence permissible value which is a permissible value of a vertical divergence of left and right eyes capable of performing stereoscopic viewing, a first unequal magnification permissible value which is a permissible value of an unequal magnification of left and right eyes capable of performing stereoscopic viewing, a second unequal magnification permissible value which is a permissible value of an unequal magnification defined in a particular direction for left and right eyes capable of performing stereoscopic viewing, a left and right eye rotation parallax permissible value which is a permissible value of a rotation parallax of left and right eyes capable of performing stereoscopic viewing.

4. The binocular visual performance measuring method according to claim 3,
wherein:
the plurality of types of closely related measurement items are the relative convergence and the left and right eye vertical divergence permissible value;
in the parallax image changing step, the left and right parallax images are shifted in a slanting direction on the display screen to approach to or depart from each other, the slanting direction being defined by combining a horizontal direction component and a vertical direction component on the display screen; and
in the measurement value calculating step, the corresponding measurement data of the relative convergence and the left and right eye vertical divergence permissible value is calculated based on the predetermine distance and a position shift amount between the left and right parallax images defined at the detected timing.

5. The binocular visual performance measuring method according to claim 4,
wherein:
the plurality of types of closely related measurement items further includes one of the first unequal magnification permissible value and the second unequal magnification permissible value;
in the parallax image changing step, display magnifications of the left and right parallax images are changed relative to each other while moving the left and right parallax images in the slanting direction on the display screen to approach to or depart from each other; and
in the measurement value calculating step, the corresponding measurement data of the relative convergence, the left and right eye vertical divergence permissible value, and one of the first unequal magnification permissible value and the second unequal magnification permissible value is calculated based on the predetermine distance and a position shift amount and a rotation angle difference between the left and right parallax images defined at the detected timing.

6. The binocular visual performance measuring method according to claim 3,
wherein:
the plurality of types of closely related measurement items are the relative convergence and the left and right eye rotation parallax permissible value;
in the parallax image changing step, at least one of the left and right parallax images is rotated about a barycenter thereof so that rotational angles of the left and right parallax images change relative to each other while shifting the left and right parallax images in a horizontal direction on the display screen to approach to or depart from each other;
in the measurement value calculating step, the corresponding measurement data of the relative convergence and the left and right eye rotation parallax permissible value is calculated based on the predetermine distance and a position shift amount and a rotation angle difference between the left and right parallax images defined at the detected timing.

7. The binocular visual performance measuring method according to claim 1, further comprising:
a distance changing step of changing the predetermined distance,
wherein the parallax image changing step, the timing detecting step and the corresponding measurement data calculating step are executed for each of the changed predetermined distances so that the corresponding measurement data of the plurality of closely related measurement items is obtained for each of the changed predetermined distances.

8. A non-transitory computer readable medium having computer readable instruction stored thereon, which, when executed by a processor of a computer for measuring binocular visual performance using a stationary 3D video monitor having a display screen on which images for enabling a subject to perform stereoscopic viewing through binocular parallax ate displayed, configures the processor to perform:
a parallax image displaying step of displaying left and right parallax images at a predetermined measurement start position on a display screen when a plurality of types of closely related measurement items of the binocular visual performance are designated;
a parallax image changing step of changing one of the left and right parallax images relative to the other of the left and right parallax images;
a timing detecting step of detecting a timing when the subject viewing the left and right parallax images from a position a predetermined distance away from the display screen becomes unable to achieve fusion of the left and right parallax images; and
a measurement value calculating step of calculating corresponding measurement data of the plurality of types of closely related measurement items respectively,
wherein:
in the parallax image changing step, one of the left and right parallax images is changed in a composite changing style in which changing patterns respectively corresponding to the plurality of types of closely related measurement items are combined;
in the measurement value calculating step, the corresponding measurement data is calculated based on the predetermined distance and a difference between the left and right parallax images defined at the detected timing; and
the corresponding measurement data represents measurement values of the plurality of types of closely related measurement items.

9. An eyeglass design method, comprising:
measuring binocular visual performance of a subject using the binocular visual performance measuring method according to claim 1; and
determining optical design values of eyeglass lenses based on a measurement result of the binocular visual performance.

10. An eyeglass lens manufacturing method, comprising:
designing eyeglass lenses using the eyeglass design method according to claim 9; and
manufacturing the eyeglass lenses according to a design result of the eyeglass lenses.

11. The binocular visual performance measuring method according to claim 1,
wherein the changing patterns include at least two of movement of the left and right parallax images in a horizontal direction, movement of the left and right parallax images in a vertical direction, enlargement or reduction of one of the left and right parallax images, change of magnification of one of the left and right parallax images in a particular direction, and a rotation of one of the left and right parallax images.

12. A binocular visual performance measuring device for measuring binocular visual performance using a stationary 3D video monitor having a display screen on which images for enabling a subject to perform stereoscopic viewing through binocular parallax are displayed, comprising:
  a parallax image displaying unit configured to display left and right parallax images for enabling a subject to perform stereoscopic viewing at a predetermined measurement start position on a display screen when a plurality of types of closely related measurement items of the binocular visual performance are designated;
  a parallax image changing unit configured to change one of the left and right parallax images relative to the other of the left and right parallax images in a composite changing style in which changing patterns respectively corresponding to the plurality of types of closely related measurement items are combined;
  a timing detecting unit configured to detect a timing when the subject viewing the left and right parallax images from a position a predetermined distance away from the display screen becomes unable to achieve fusion of the left and right parallax images; and
  a measurement value calculating unit configured to calculate corresponding measurement data of the plurality of types of closely related measurement items respectively based on the predetermined distance and a difference between the left and right parallax images defined at the detected timing, wherein the corresponding measurement data represents measurement values of the plurality of types of closely related measurement items.

13. A binocular visual performance measuring device for measuring binocular visual performance, the method comprising:
  a parallax image displaying unit configured to display left and right parallax images for enabling a subject to perform stereoscopic viewing at a predetermined measurement start position on a display screen of a 3D video monitor when a plurality of types of closely related measurement items of the binocular visual performance are designated;
  a parallax image changing unit configured to change one of the left and right parallax images relative to the other of the left and right parallax images;
  a timing detecting unit configured to detect a timing when the subject viewing the left and right parallax images from a position a predetermined distance away from the display screen becomes unable to achieve fusion of the left and right parallax images; and
  a measurement value calculating unit configured to calculate corresponding measurement data of the plurality of types of closely related measurement items respectively,
  wherein;
  the parallax image changing unit is configured to change one of the left and right parallax images in a composite changing style in which changing patterns respectively corresponding to the plurality of types of closely related measurement items are combined;
  the measurement value calculating unit is configured to calculate the corresponding measurement data based on the predetermined distance and a difference between the left and right parallax images defined at the detected timing; and
  the corresponding measurement data represents measurement values of the plurality of types of closely related measurement items.

14. The binocular visual performance measuring method according to claim 1,
  wherein:
  the measurement value calculating step further comprises performing a composite measurement in which the plurality of types of closely related measurement items are measured simultaneously.

15. The binocular visual performance measuring method according to claim 14,
  wherein:
  the measurement value calculating step further comprises receiving selected measurement items to be measured simultaneously in the measurement value calculating step.

16. The binocular visual performance measuring method according to claim 14,
  wherein:
  the plurality of types of closely related measurement items are closely related to each other with respect to eye positions.

* * * * *